(12) United States Patent
Powell et al.

(10) Patent No.: US 7,019,829 B2
(45) Date of Patent: *Mar. 28, 2006

(54) METHOD AND DEVICE UTILIZING PLASMA SOURCE FOR REAL-TIME GAS SAMPLING

(75) Inventors: Gary Powell, Petaluma, CA (US); Richard L. Hazard, Lafayette, CA (US)

(73) Assignee: Lightwind Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/939,637

(22) Filed: Sep. 13, 2004

(65) Prior Publication Data

US 2005/0030531 A1    Feb. 10, 2005

Related U.S. Application Data

(63) Continuation of application No. 10/038,090, filed on Oct. 29, 2001, now Pat. No. 6,791,692, which is a continuation-in-part of application No. 09/726,195, filed on Nov. 29, 2000, now Pat. No. 6,538,734.

(51) Int. Cl.
*G01J 3/30*     (2006.01)
*G01N 21/73*    (2006.01)

(52) U.S. Cl. .......................... 356/316; 438/16
(58) Field of Classification Search ................ 356/72, 356/316; 438/16
See application file for complete search history.

(56) References Cited

U.S. PATENT DOCUMENTS

| | | | |
|---|---|---|---|
| 3,734,631 A | 5/1973 | Justice et al. | |
| 4,147,431 A | 4/1979 | Mann | 356/72 |
| 4,148,612 A | 4/1979 | Taylor et al. | |
| 4,309,187 A | 1/1982 | Dodge, III et al. | |
| 4,609,426 A | 9/1986 | Ogawa et al. | 156/626 |
| 4,847,792 A | 7/1989 | Barna et al. | 364/552 |
| 4,857,136 A * | 8/1989 | Zajac | 438/16 |
| 4,859,277 A | 8/1989 | Barna et al. | 156/626 |
| 5,273,610 A | 12/1993 | Thomas, III et al. | 156/345 |
| 5,326,975 A | 7/1994 | Barna | 250/372 |
| 5,473,162 A | 12/1995 | Busch et al. | |
| 5,546,322 A | 8/1996 | Gifford et al. | 364/497 |
| 5,857,890 A | 1/1999 | Ferran | 445/67 |

(Continued)

FOREIGN PATENT DOCUMENTS

JP    58084431 A    5/1983

OTHER PUBLICATIONS

Danner et al. *Downstream Atomic Monitoring for Absolute Etch Rate Determinations* J. Electrochem. Soc: Solid-State Science and Technology Apr. 1983.

(Continued)

*Primary Examiner*—F. L. Evans
(74) *Attorney, Agent, or Firm*—Ernest J. Beffel, Jr.; Haynes Beffel & Wolfeld LLP

(57) ABSTRACT

Aspects of the present invention provide novel methods and devices for sampling gas, exciting the sampled gas to emit radiation and detecting in real time from the emitted radiation a plurality of wave bands of an emission spectrum. Energy used to excite the sampled gas may be adjusted based on the detected wave bands. A process may be controlled in real time based on the detected wave bands. Novel interfaces may be used to display portions of the detected wave bands. A known flow of a reference gas may be included in the flow of sampled gases and an unknown flow of an unknown flow gas determined.

21 Claims, 18 Drawing Sheets

U.S. PATENT DOCUMENTS

| | | | |
|---|---|---|---|
| 5,877,032 A | 3/1999 | Guinn et al. | 438/9 |
| 5,949,193 A | 9/1999 | Roine et al. | 315/111.51 |
| 5,963,336 A | 10/1999 | McAndrew et al. | 356/437 |
| 5,986,747 A * | 11/1999 | Moran | 356/72 |
| 6,045,618 A | 4/2000 | Raoux et al. | 118/715 |
| 6,046,796 A | 4/2000 | Markle et al. | 356/72 |
| 6,068,783 A | 5/2000 | Szetsen | 216/60 |
| 6,134,005 A | 10/2000 | Smith, Jr. et al. | 356/346 |
| 6,366,346 B1 * | 4/2002 | Nowak et al. | 356/72 |
| 6,643,014 B1 | 11/2003 | Chevalier et al. | |

OTHER PUBLICATIONS

Lichtman *Residual Gas Analysis: Past, Present and Future* J. Vac. Sci. Technol. A 8 (3) May/Jun. 1990, 1990 American Vacuum Society.

* cited by examiner

METHOD AND DEVICE UTILIZING PLASMA SOURCE FOR REAL-TIME GAS SAMPLING

RELATED APPLICATION DATA

This application is a continuation of application Ser. No. 10/038,090, filed 29 Oct. 2001 and issuing on 14 Sep. 2004 as U.S. Pat. No. 6,791,692; which application is a continuation-in-part of application Ser. No. 09/726,195, filed 29 Nov. 2000, issued on 25 Mar. 2003 as U.S. Pat. No. 6,538,734.

BACKGROUND OF THE INVENTION

1. Field of the Invention

The present invention relates real-time gas sampling and spectral analysis.

2. Description of Related Art

Semiconductor manufacturing has adopted various telemetry techniques utilizing mass spectrometry or spectrographic analysis to improve the cleaning, conditioning or operation of reaction chambers in which a variety of reactions take place, such as deposition, cleaning, etching, implantation, ashing, etc. Telemetry techniques help operators monitor processes which take place on a microscopic level inside a closed chamber which often is sensitive to any form of outside radiation.

SUMMARY OF INVENTION

One aspect of the present invention includes sampling gas outside a reaction chamber that has passed through the reaction chamber during a process, wherein the gas diffuses into an excitation chamber. In the excitation chamber, exciting the sampled gas, using at least one external electrode, to emit radiation. And, detecting in real time from the emitted radiation a plurality of wave bands of an emission spectrum. Energy used to excite the sampled gas may be adjusted based on the detected wave bands. A process may be controlled in real time based on the detected wave bands. Novel interfaces may be used to display portions of the detected wave bands. A known flow of a reference gas may be included in the flow of sampled gases and an unknown flow of an unknown flow gas determined. Other aspects of the present invention are set forth in the figures, detailed description and claims.

DETAILED DESCRIPTION

The following description of various aspects and embodiments of the invention is presented for purposes of illustration and description. The description is not intended to limit the invention to the precise forms disclosed. Many modifications and equivalent arrangements will be apparent to people skilled in the art.

Figure 1:
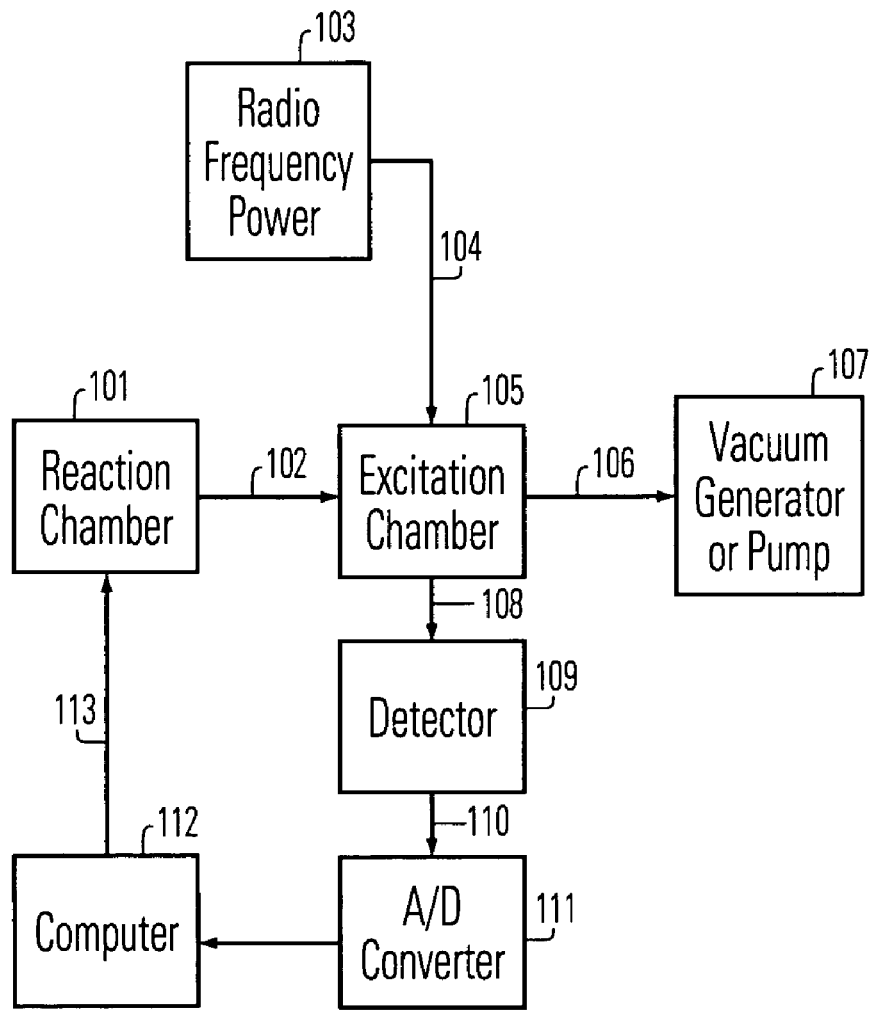
FIG. 1 is a schematic diagram of a system practicing aspects of the invention.

FIG. 1 shows a schematic overview of a system including a useful plasma source and a detector. Gas samples from a reaction chamber 101 are communicated 102 to an excitation chamber 105. The process in the reaction chamber broadly may include a calibration of gas flow through mass flow controllers, checking for a leak or any of a variety of reactions, such as deposition, cleaning, etching, implantation, ashing, etc. The communication of sampled gas may correspond to one or more exhaust streams from the reaction chamber or any other outlet from the reaction chamber. The sampled gas may be representative of material supplied to the reaction chamber, plasma created in the reaction chamber, or exhaust gas containing byproducts of a reaction taking place in the reaction chamber; alternatively, the gas need not be representative, but should have a reproducible relationship to some factor of interest.

The excitation chamber 105 is connected by a cable 104 to a radio frequency power source 103. The excitation chamber 105 may be capacitively or inductively coupled to the sampled gas. Alternatively, a system could practice aspects of the present invention utilizing microwave or cyclotron radiation, or utilizing internal electrodes such as arc electrodes to excite the sampled gas to a plasma state in which it emits radiation. In FIG. 1, the sampled gas is drawn through or past the excitation chamber 105 by communication 106 with a vacuum generator or pump 107. The sampled gas may reach the excitation chamber 105 by direct flow through the chamber or by diffusion into the chamber.

The sampled gas in the excitation chamber 105 is excited to emit radiation. The emitted radiation comprises an emission spectrum of the sampled gas. The emitted radiation passes through a window or fiber optic cable 108 to a plurality of detectors 109 which are responsive in real time to wave bands of the emitted spectrum. Several modifications to a simple window, not depicted in the figure, can improve the durability of the system. Control logic can be provided to activate a self-cleaning plasma cycle using the plasma source can keep the window clean. This approach is similar to a mini-clean in a reaction chamber. Either $N_2$ purge gas or spilled $O_2$, or gases from a non-process gas source can be used to generate a suitable plasma to clean the window. Injection of gas into the source or in front of the window can facilitate self-cleaning or even prevent accumulations on the window. Gas can be injected between processing cycles, the timing based on evaluation of SECS message traffic. Alternatively, heat can be applied to one or more vacuum lines or to the plasma source to prevent deposition of unwanted material on the window. In addition, the window leading to the fiber optic cable may be implemented as a disposable and easily replaced component, so that any failure of other measures to keep the window clean can be remedied with a simple replacement. A SMA 905 to single strand optical fiber connector (0.22 NA) may be used. In an alternative embodiment, a right angle, front surface mirror can be used at the window to change the lead of the optical fiber into the device. A focusing element can be used in either embodiment to match the signal through the window to the cross-section of the optical fiber. The individual detectors may be photomultiplier tubes, photodiodes, CCD's or other photosensitive components. The individual detectors may be characterized as shallow junction or deep junction devices. A useful characteristic of detectors is quick response time, permitting a scan and A/D conversion of signals from a plurality of detectors in 20 milliseconds or less, which can presently be attained by using shallow junction devices such as shallow junction CCD's. The respective detectors will be sensitive to a plurality of wave bands of the emitted radiation. This may be accomplished by positioning the respective detectors to receive diffracted light from a diffraction grating, by using filters, or by equivalent means. A plurality of detectors receive energy received in their respective wave bands at substantially the same time, though the sensitivity of individual detectors to particular wave bands may be increased by varying the integration time among the respective detectors.

A useful configuration of detectors and a diffraction grating includes spacing the detectors in relation to the diffracted light so the detectors are responsive to band widths sufficiently narrow that a plurality of detectors are responsive to a single peak in an emission spectrum. A prepackaged device capable of focusing detectors on wave bands of 1.23 nm FWHM bandwidth is a Sony ILX511 device. In an alternative embodiment, a Sony device with a USB interface can be used. Either Sony device includes a 2,048 detector CCD array and a diffraction grating. Individual elements are 12.5 mm×200 mm. The well depth of an individual element at 600 nm is 160,000 photons. The estimated sensitivity may be expressed as 86 photons/count, $2.9 \times 10^{-17}$ joule/count, or $2.9 \times 10^{-17}$ watts/count for 1-second integration. Its effective range is 200–1000 nm and its integration time may be 3 ms with a 1 MHz A/D card or 4 ms with a 500 kHz A/D card. The Sony IXL511 device can be configured with a grating which diffracts radiation in the 200 to 850 nm spectrum. A slit of 25 mm is typical, with 10, 50 and 100 mm slits available. Various combinations of groove density, fiber diameter and slit width can be selected for additional sensitivity or a wider spectral range. Optics suitable to UV radiation in the 200–350 nm range are used. Order sorting is accomplished with a single-piece, multi-bandpass detector coating for applications in the 200–850 nm spectrum. Detector enhancements which increase UV sensitivity are susceptible to false signals at shorter wavelengths. A coating is used to reduce the effects of wavelengths that are second or third harmonics of the signal of interest. A scan time for collecting and converting data from the array elements is 20 milliseconds or less. In a cost sensitive application, a more modest array having 1024 or 512 detectors can be used. In an even more cost sensitive application, a plurality of detectors can be used, either with a diffraction grating or with filters which effectively tune the respective detectors to specific wave bands or wave lengths.

Elements of the detector 109 typically are wired 110 to an analog to digital (A/D) converter 111. The output of the A/D converter 111 is connected to a computer 111. When the A/D converter is an A/D card and the computer is a PC or workstation, the connection may be by PCI bus or other bus. A 300 MHz or faster PC with 64 megabytes RAM, a CD-ROM drive, memory for storing programs which operate and control the sampling, exciting and detecting apparatus, and a modem may be equipped with Windows 98 Second Release and Labview 6.1 software. Later versions or alternatives to these OS and data collection software can be used. Custom software provides user and device interfaces. The computer 112 can communicate 113 with controllers for the reaction chamber 101. The computer can control process parameters for the reaction chamber directly, as depicted, through another computer or controller, or by providing data to an operator who controls the process parameters. The computer also can store data collected during operation of the process for later analysis. A further use of the computer, understandable by reference to FIG. 1, is to control the energy used to excite the sampled gas to emit radiation. In some instances, the energy used can be reduced to avoid or reduce saturation of detectors responsive to particular wave bands. In other instances, the energy used can be increased to increase the radiation emitted in particular wave bands.

Figure 2:
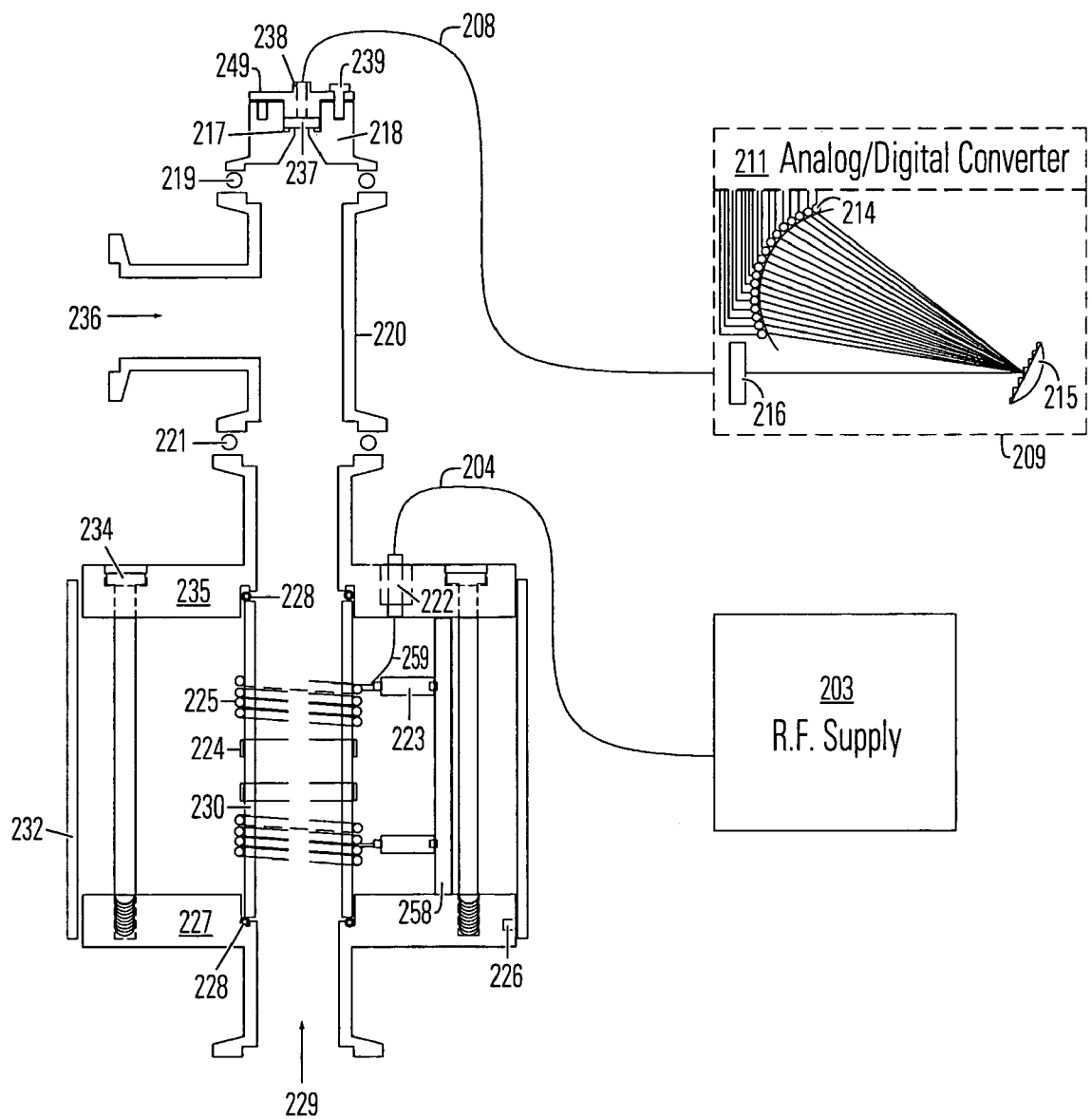
FIG. 2 depicts one configuration of a useful plasma source and detector.

FIG. 2 depicts one configuration of a useful plasma source and detector. This plasma source is inductively and capacitively coupled to the sampled gas in the excitation chamber. With various kinds of shielding, the mode of coupling can be limited. FIG. 2 is a cross-section view. A vacuum "T" 220 connects the reaction chamber (not shown) to an apparatus which excites sampled gas and detects the emitted radiation. The vacuum "T" 220 is connected to the reaction chamber at 236. This connection can be to an exhaust from the reaction chamber or a manifold connecting a plurality of exhausts. Alternatively, this connection can be to at least one sampling port or at least one feed line. At one end, the source input cap 235 is attached to the vacuum "T" 220. A compressible o-ring 221 isolates the sampled gas from ambient gas surrounding the apparatus. The sampled gas typically is at a low pressure, measured in torrs or millitorrs. Effective isolation is provided from ambient gas surrounding the apparatus, which may be atmospheric gas or a clean room gas. The vacuum "T" 220 also is connected to an optical vacuum blank 218, with an additional compressible o-ring 219. A pressure differential between inlet 236 and outlet 229 produces a flow of sampled gas through the excitation chamber 230. When the inlet is connected to at least one exhaust from the reaction chamber, at least a portion of the exhaust gas from the reaction chamber flows through the excitation chamber.

The apparatus which excites gas includes the inlet cap 235, an excitation chamber 230 and an outlet cap 227. O-rings 228 are positioned between the excitation chamber and the caps. Bolts 234 compress the O-rings and secure the caps. A covering 232 surrounds the body of this apparatus. An R. F. power supply 203 is connected by a cable 204 through a bulkhead connector 222 to a connector wire 259. A support 258 positions capacitors 223 which are connected to the connector wire 259, the coil 225 and the external igniter rings 224. In an alternative configuration, an internal igniter exposed to sampled gas in the excitation chamber. 230 could be used. In one embodiment, the R. F. power supply 203 broadcasts at 13.56 MHz. This R. F. energy passes through the capacitor 223 into the coil 225 and ignition rings 224. An electrical discharge in the excitation chamber results, causing the sampled gas to emit radiation. To improve power transfer efficiency, a matching network may be added to the source. The impedance of the gases before ignition or initiation of the plasma state is different than after ignition. The igniter bands 224 can be used to capacitively ignite the plasma. The capacitors 223 are charged to a sufficient voltage to break down the gas in the excitation chamber 230. When ignition occurs, the impedance changes and power transfer occurs through the inductive coils 225. A capacitor can be used to adjust the reactance of the circuit. Power can be shunted through a resistor to ground. The combination of passive capacitive and resistive components broadens the effective impedance range through which power can effectively be coupled into the sampled gas. When the sampled gas transitions to a plasma state, its volume changes as a function of the R. F. power input. As the power increases, the gas breakdown and ion generation increase; radiation is emitted. The applied R. F. power for exciting the sampled gas to emit radiation is independent of any plasma source for the reaction chamber.

At the optical vacuum blank 218, a group of screws 239 compress an optical adapter 249 against a window 237 and O-rings 217. The window 237 can be made of sapphire which transmits light from approximately 200 nm into the near infrared region, such as 850 or 1000 nm. The optical adapter 249 mechanically supports a fiber optic connector 238 which provides a quick connection to fiber optic cable 208. The fiber optic cable 208 transmits radiation emitted by the sampled gas to detector 209. Light emerging from the cable 208 enters the detector 209 through a lens 216 which focuses it on a diffraction grating 215. The grating 215 separates the light into a spectrum which is diffracted in an orderly fashion across a detector array 214. The detector array 214 converts photons into electrical energy, generating analog signals proportional to the intensity of photons in the wavebands on which the respective detectors are focused. In alternative embodiments, individual detectors may be located so that they are responsive to specific diffracted wavebands or individual detectors may be equipped with filters so that no diffraction grating is required. An analog to digital converter 211 is connected to the detectors. It scans the detectors and converts their analog outputs to digital signal.

Figure 3:
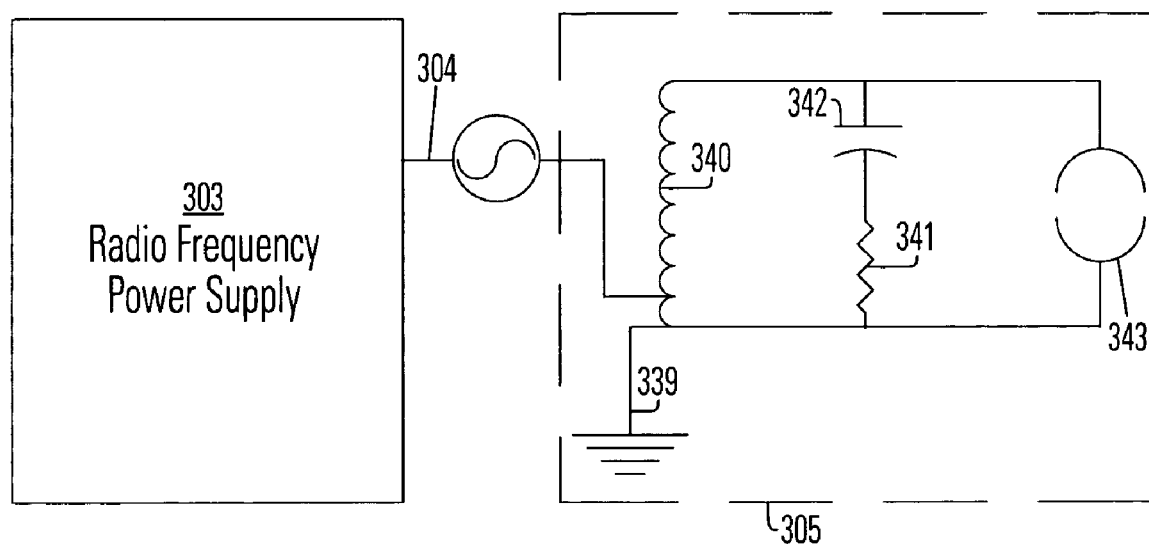
FIG. 3 is a simplified schematic view of a radio frequency power supply and power transfer section.

FIG. 3 is a simplified schematic view of a radio frequency power supply and power transfer section. An R. F. power supply 303 generates an R. F. signal which is coupled 304 to a power transfer section 305. The power transfer section comprises a coil or inductor 340, a resistor 341, a capacitor 342, ignition rings 343 and a ground 339. The ignition rings function as a capacitor under certain conditions.

Figure 4:
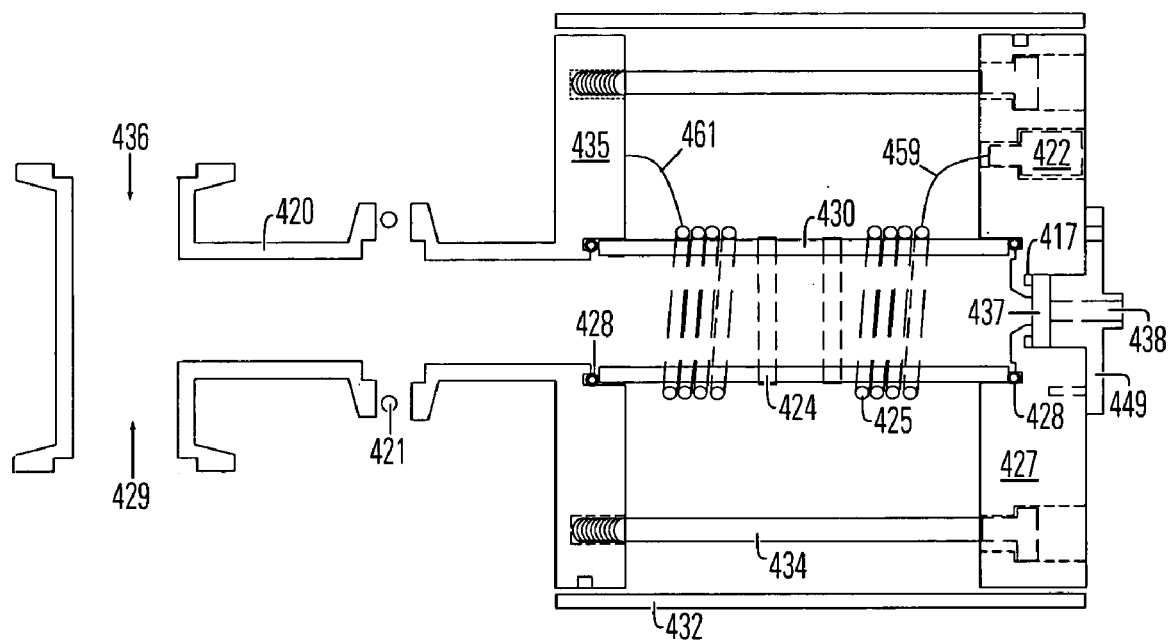
FIG. 4 is an alternate configuration of a useful plasma source and optical fiber connector.

FIG. 4 is an alternate configuration of a useful plasma source and optical fiber connector. In this configuration, the vacuum "T" allows sampled gas to diffuse through the excitation chamber, rather than flowing through it. The numbering of elements in FIG. 4 generally corresponds to the numbering of elements in FIG. 2. A pressure differential causes gas to flow from the inlet 436 to outlet 429. Gas diffuses through the connector 420 and inlet cap 435 into excitation chamber 430. Isolation from ambient gas is maintained and various junctures by O-rings 421, 428 and 417. The inlet cap 435 is compressed against the excitation chamber 430 and the optical adapter cap 427 by bolts 434. An R. F. bulkhead adapter 422 receives an R. F. signal and communicates the signal along connector wire 459 to a coil 425. In this figure, charging capacitors for the igniter rings 424 are not depicted. A ground wire 461 connects to the coil or inductor 425. The optical vacuum blank 449 is secured against a window 437. It includes an optical fiber connector 438. A covering 432 surrounds this portion of the apparatus. The configuration in FIG. 4 is adapted to a different gas flow than the configuration in FIG. 2. For production purposes, the similar components may be used in the two configurations.

Positioning a device at the exhaust of a reaction chamber tends to isolate the externally generated plasma and the detectors from the confounding effect of rotating or pulsating energy used to generate plasma in some reaction chambers. Both TEL and Applied Materials, for instance, have produced plasma devices that use rotating magnetic fields. When a varying energy source generates plasma, a strong variation in intensity appears across the whole spectrum. Sampling reactor exhaust and generating an external plasma combine to yield relatively stable intensity of emissions from the plasma. Positive feedback to the plasma source can yield a more stable intensity and, if needed, counteract the effect of the rotating or pulsating energy in the reaction chamber.

Figure 5:
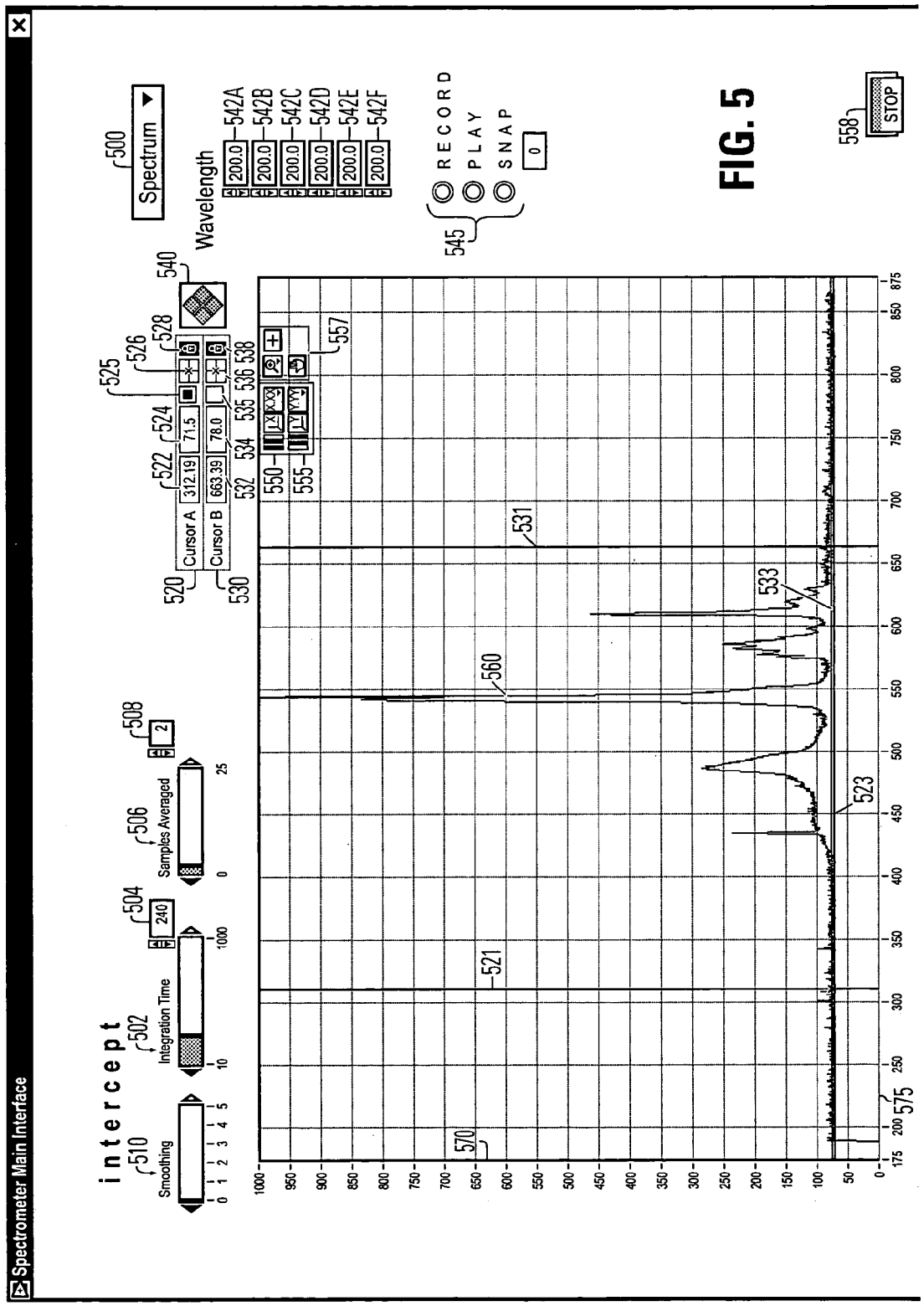
FIGS. 5–8 are interfaces between the user and a system utilizing aspects of the present invention.

FIG. 5 depicts a graphical interface which practices aspects of the present invention. This is the "spectrum" interface, selected using a pull down list 500. Certain interface controls are common to this and other interfaces. Integration time for producing integrated detections may alternately be controlled by dragging a slide bar 502 or entering a value 504. The integration time controls the accumulation and reset of charges in the individual detectors. In this figure, a single integration time is depicted. Alternatively, the integration time could vary across wavebands of a spectrum of emitted radiation, to compensate for variable sensitivity of detectors across wavebands or to produce a greater signal gain in portions of the spectrum where faint peaks are expected. The interface control for integration time would then be a scaling factor, rather than a number of milliseconds. The number of integrated detections to be averaged together may alternately be controlled by dragging a slide bar 506 or entering a value 508. The samples averaged are the number of samples which are averaged produce a point of data for display. In this interface embodiment, sampling of 1 to 25 integrated detections is depicted. Smoothing is controlled by a slide bar 510. Many types of smoothing can be applied, such as boxcar and moving average smoothing. This interface embodiment depicts smoothing factors in the range of 0 to 5. Cursor controls 520 and 530 also are common among interfaces. Two separate cursors are provided in this embodiment. Placement of the cursor is controlled by the user when the cursor tool 526, 536 is active and the cursor lock 528, 538 is inactive. Controls 525 and 535 turn on either or both cursors or crosshairs displayed on the screen. Those crosshairs are moved by selecting and dragging, or by incremental stepping with control 540. As a user drags the cursor to a location, numeric readouts are displayed for wavelength 522, 532 along the x-axis 575 and a measure of intensity 524, 534 along the y-axis 570. The crosshairs corresponding to cursor A appear as lines 521 and 523; the crosshairs for cursor B are lines 531 and 533. Control 540 steps the selected crosshairs left, right up or down in increments of one pixel. Wavelength selection 542A-E also is common to several interfaces, but is not active for the "spectrum" interface, because no single wavelength is tracked or graphed. In other interfaces, the user may select six different wavelengths to track. The number of wavelengths tracked is somewhat arbitrary, up to the limits of the screen layout and the hardware capabilities of the detector, converters and computer system. Eight wavelengths or more also may be tracked, up to and including the number of detectors. The stop button 558 is shared among interfaces. Controls 550, 555 and 557 also are common. Controls for the x-axis 550 and y-axis 555 set the range covered by the respective axises and the format of the axis labels. Mouse cursor controls 557 control zooming, centering and repositioning the display. Particular to the "spectrum" interface are button controls 545 and the line graph 560 depiction of the detected spectrum of emitted radiation from the excited sampled gas.

In addition to averaging samples over time and integrating samples across multiple detectors under a single peak, samples can be accumulated across multiple peaks associated with a chemical of interest. From a spectrum as appears in FIG. 6, multiple peaks can be taken together. For instance, CN peaks centered at about 386 nm and 664 nm can be treated collectively or CO peaks centered at about 483 nm and 520 nm can be combined into one signal for processing. In general, the fine resolution of detectors, the numerous detectors and the storage of multiple samples taken in a short time allow application of numerical techniques that enhance the effective signal to noise ratio. The numerical techniques include integrating multiple detectors under a single peak, averaging across samples and combining multiple peaks associated with a single chemical. In practice, it has been observed that practicing aspects of the present invention yields better reaction endpoint detection than using a photodetector and filter combination to reads emissions through a window from a reactor chamber.

Figure 6:
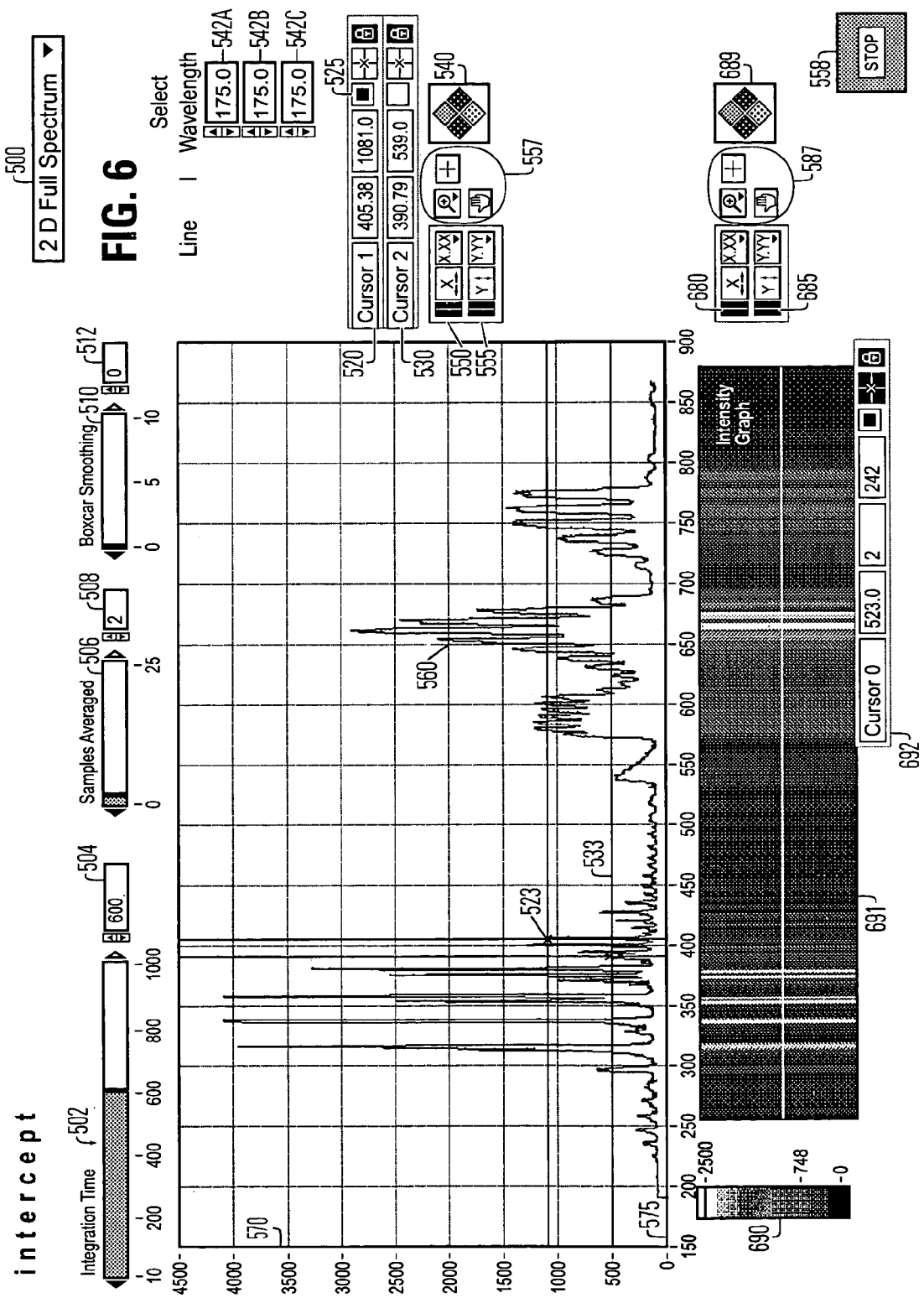

FIG. 6 depicts the "2 D full spectrum" interface. This interface includes the line graph and numerical readouts of the "spectrum" interface, plus an intensity graph. The numbering of interface elements in FIG. 6 is repeated from FIG. 5, to the extent applicable. Differences include fewer (still inactive) wavelength selection options 542A–C and a numerical smoothing selection control 512, in addition to the slider smoothing selection control 510. The intensity graph 691 appears in this embodiment as a bright line spectrum, wherein peaks of spectral intensity are represented by light colors. In a full color display, a range of dark blue to white or any other color range could be substituted for black to white. An alternative display could be in a dark line format. The bright line format is preferred, because it is more commonly used for emission spectrums, whereas the dark line format is used for absorption spectrums. An intensity scale 690 is provided. This intensity scale may top out or saturate at a different value than the top intensity value for the line graph. Controls for the x-axis 680 and the y-axis 685 correspond to controls 550 and 555. Mouse cursor controls 687 and 689 correspond to 557 and 540. The Cursor 0 controls 692 generally correspond cursor 1, 2 controls 520, 530. Controls 687 include a hand which moves the graph around. The magnifying glass invokes a pop-up menu that allows zooming in or out on selected portions of the graph. Control 689 has the same effect as control 540. The line graph and intensity graph provide a pair of readouts for spectral data, complemented by the additional numerical readouts associated with the cursors.

A scan of the full spectrum can be implemented to search for anomalies. Keyed to the production process, a profile of expected peaks, error indicating peaks or good and bad historical spectra can be loaded into software. One way of keying the analysis to the production process is to listen to SECS messages to and from the reaction chamber. A listening post device available from EquipNET™ can be used to detect and interpret SECS messages in real time, without disrupting communications. The SECS messages can be correlated with processing. One technique for detecting anomalies is to integrate portions of the full spectrum into peaks. These peaks may be described by centers, areas and widths, or by focal points, average amplitudes, and standard deviations. These peaks and ratios of these peaks can be compared to a profile of expected peaks. Both unexpected peaks and missing peaks can be reported and acted upon. These peaks and ratios of these peaks also can be compared to error indicating peaks and the error indicators can be reported or acted upon. The actions may include terminating a process, modifying process parameters or modifying subsequent steps in a multi-step process. Another technique for detecting anomalies is to calculate one or more differences between historical spectra and a production spectrum. Then, the resulting spectrum difference can be analyzed and reported or acted upon. Both peaks and ratios of peaks can be calculated and compared to a profile. Reporting and actions can either be based on raw data or follow rules in a rule database.

Figure 7:
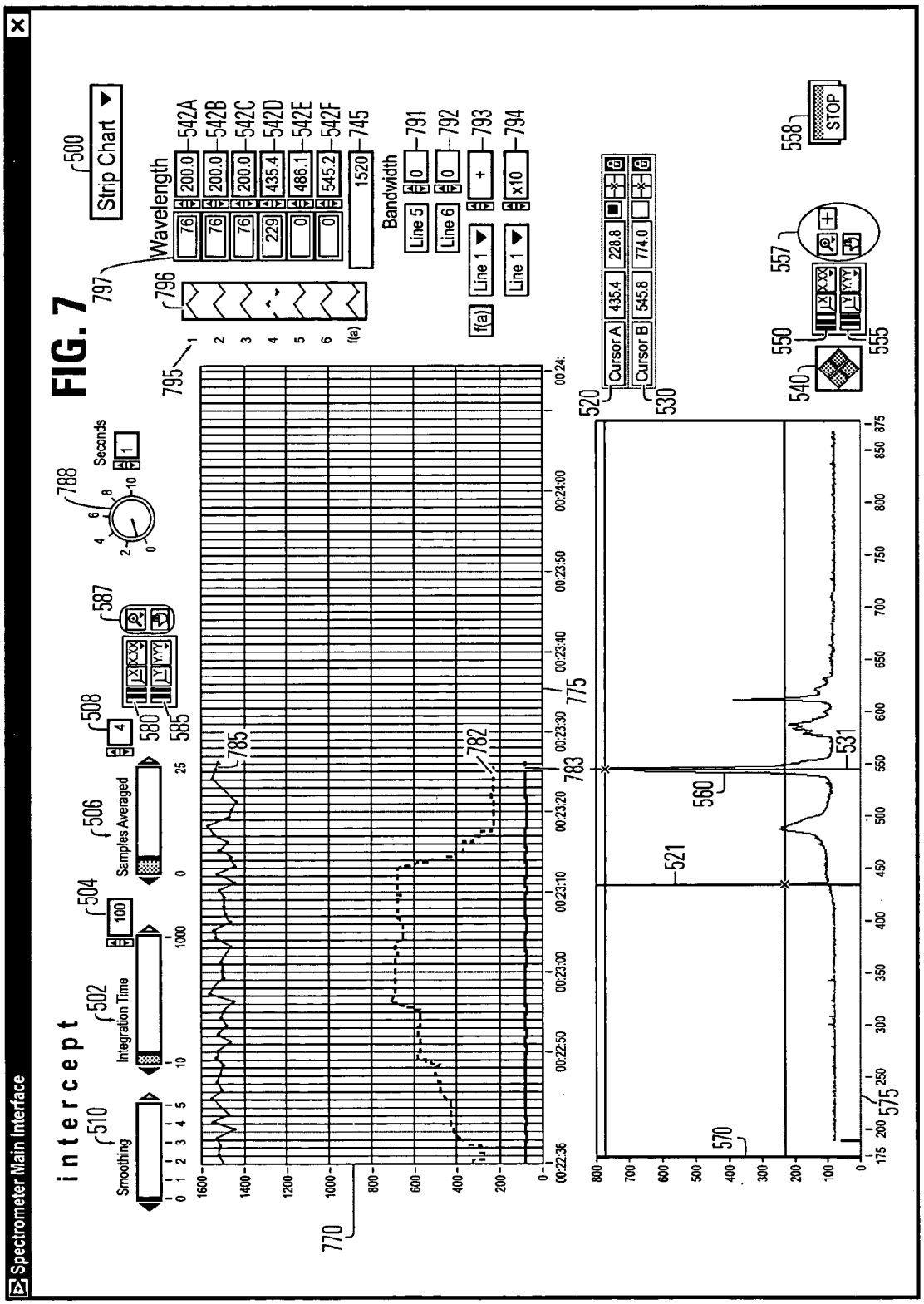

FIG. 7 depicts a "strip chart" interface, which combines readout features of the "spectrum" interface in FIG. 5 with a strip chart and algebraic function readout. The numbering for the spectrum display in the lower half of FIG. 7 corresponds to the numbering of FIG. 5. A number of elements are added for the strip chart display in the upper half of FIG. 7. A seconds control 788, including an indicator knob and a numeric entry window control the x-axis (775) of the strip chart. The wavelength selector controls 542A–F are operative for the strip chart. Complementary to these controls are a spectral line number 795, a color legend 796, and a current intensity value for each of the spectral lines. Controls 542 select the wavelengths that will be tracked on the strip chart recorder graph 720. The numeric intensity readout for each line is the 797 column. Note that the intensity values of 0 correspond to a bandwidth of 0 for spectral lines 5, 6. The intensity values of 76 correspond to background levels for spectral lines 1–3. The spectral line number f(a) and related controls 745 are for a function of other selected spectral lines or wavebands. Bandwidths for selected spectral lines are directly controllable 791, 792. A displayable function f(a) of two selected spectral lines or wavebands can be constructed using controls 793 and 794. This embodiment depicts an algebraic combination of the form x +ay, where a=10. Alternatively, any other algebraic function could be displayed. For instance, a derivative function, tracking the slope of a spectral line over time or the curvature of a spectral line could be tracked. In FIG. 7, strip chart line 782 corresponds to spectral line 4 (542D). Line 783 corresponds to spectral line 1 (542A) and line 785 corresponds to f(a) (793+794), which, as depicted, is 11 times the magnitude of spectral line 1 (542A).

Figure 8:
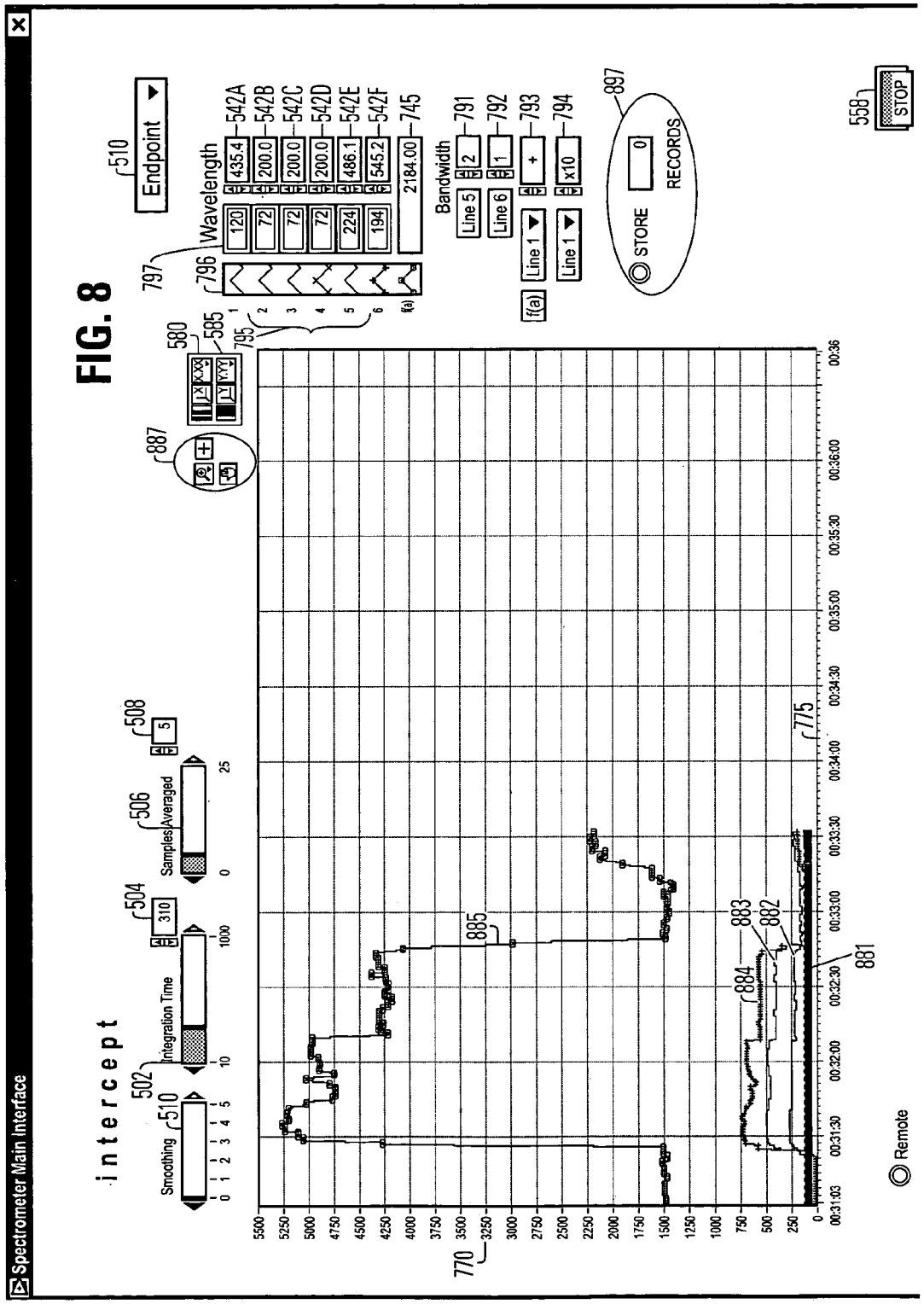

FIG. 8 depicts an "endpoint" interface which includes the readout features of the top half of the "strip chart" interface of FIG. 7. In this figure, line 881 corresponds to the background levels of spectral lines 2–4. Line 882 corresponds to spectral line 1. Line 883 corresponds to spectral line 5. Line 884 corresponds to spectral line 6. Line 885 corresponds to spectral line f(a) (745). A button is added to this interface to allow a user to trigger storage of a specified number of records 897.

Figure 9:
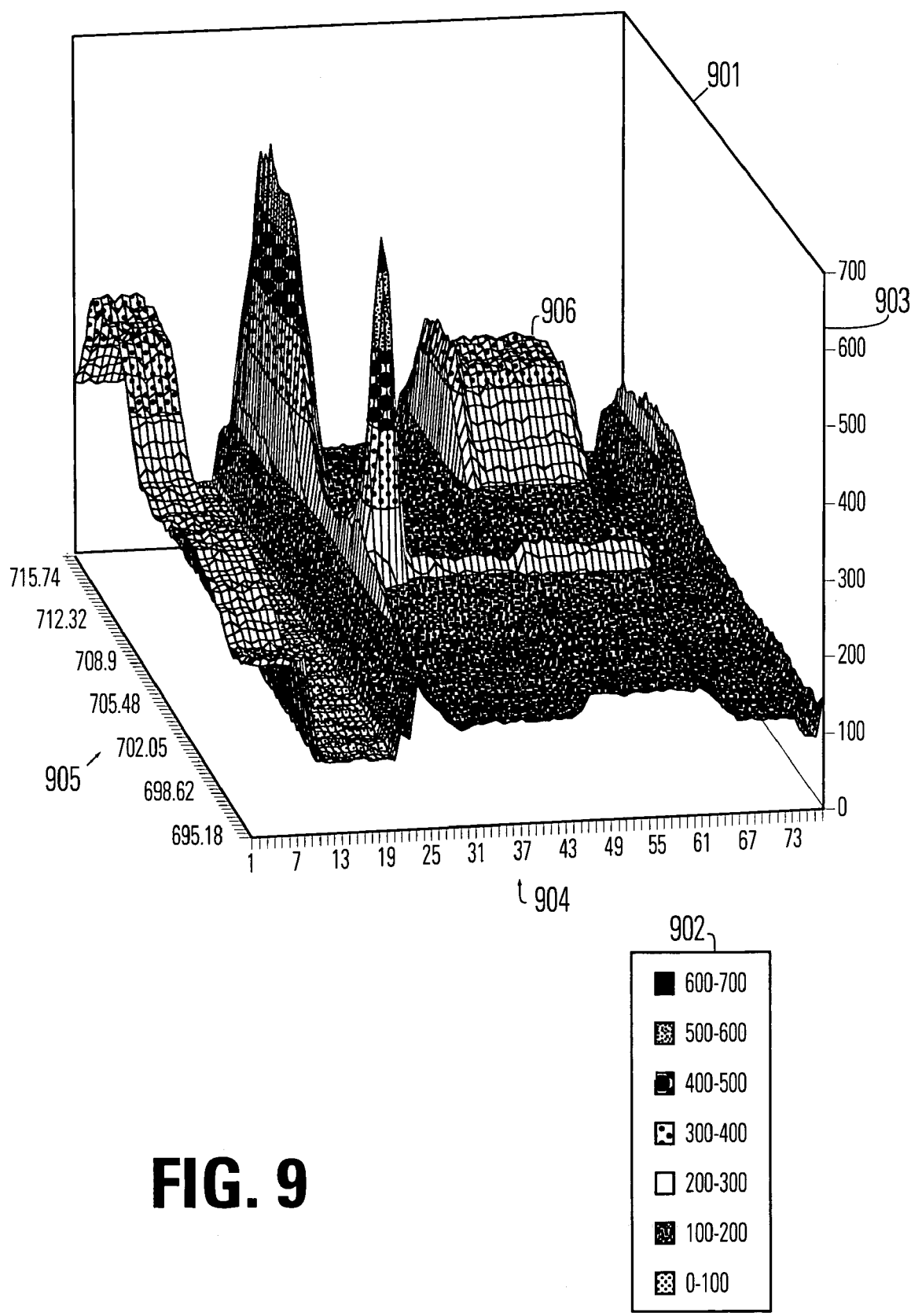
FIG. 9 depicts a 3-D map of gas changes through a full nitride etch cycle.

Records saved from the spectral history of a process can be analyzed as shown in FIG. 9. The three dimensional presentation of this data is framed 901. The legend 902 assigns colors to different levels of intensity. Z-axis scale 903 is a measure of emitted radiation intensity in each of the wave bands. X-axis scale 904 corresponds to time. Y-axis scale 905 corresponds to wavelengths of measured radiation. The shaded wire frame 906 presents the data.

The data in FIG. 9 shows a portion of the emission spectrum, from 695 to 718 nm wavelengths, for a full nitride etch cycle. This 3D presentation assists an operator in understanding changes in reaction byproducts produced during the etch. Key wavelengths to monitor can be identified and characteristic rises and falls in emission intensity can be gauged. Straight forward review of this or a similar data presentation can enable an operator to set parameters for an endpoint process control for this nitride etch cycle or another process.

Figure 10:
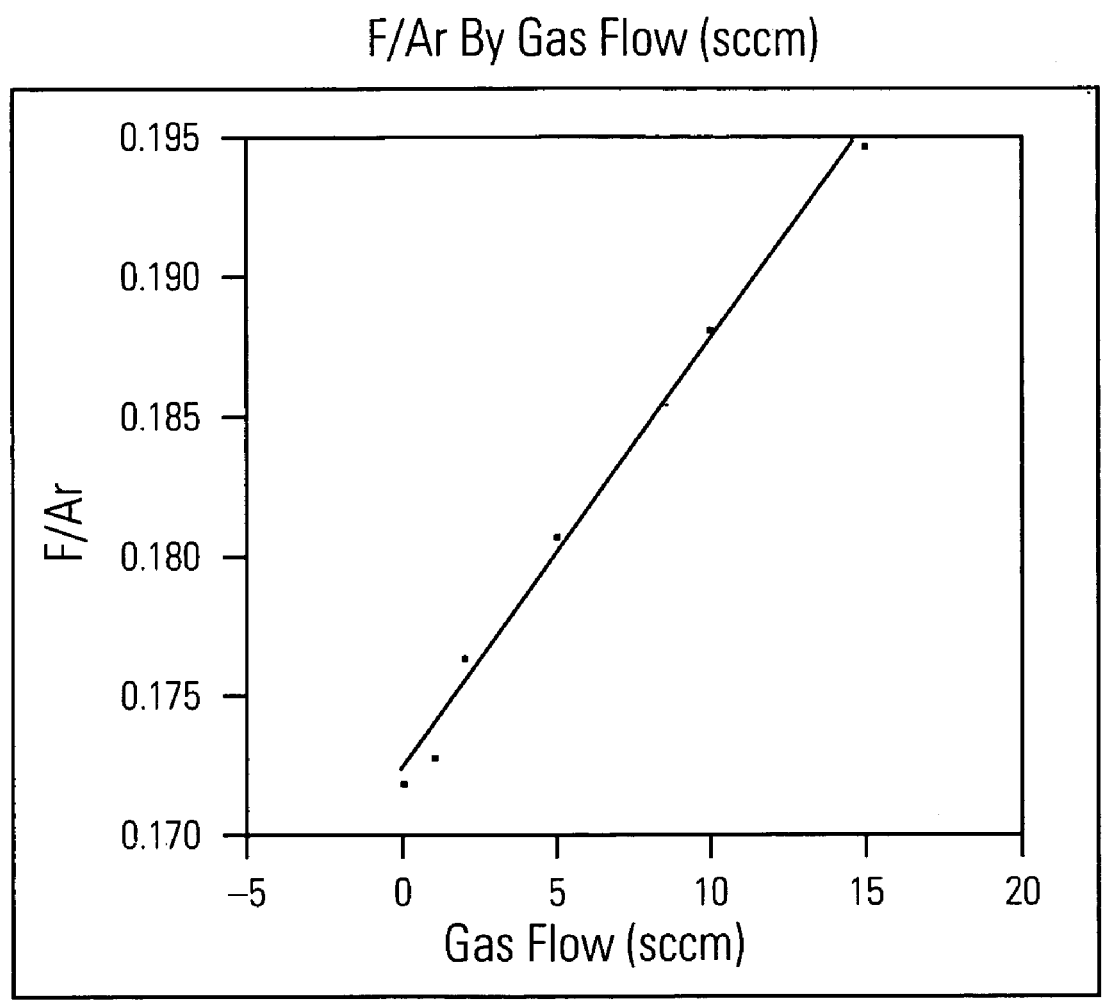
FIG. 10 graphs results of calibration tests for introducing a reference gas to the gases exhausted from a reaction chamber.

FIG. 10 depicts a process in which a reference gas is used to determine quantitatively the amount of fluorine in an exhaust stream. The peaks analyzed were fluorine at 704 nm and argon at 750 nm. The data in this figure are from tests run on a Lam XL etcher, using gas flow but no plasma discharge in the reaction chamber. A gas flow including 500 scam argon was initiated. Varying quantities of $CF_4$ gas, from 1 to 20 scam, were introduced. By flow, the fluorine was sometimes less than 0.002 percent of the total flow. With stable flows, peaks for fluorine and argon were measured. A ratio of the measured intensities of the peaks F(704)/Ag (750) was calculated for each quantity of $CF_4$ gas. The ratios were graphed in FIG. 10. Linear regression was used to fit the ratios. The following table summarizes the fit:

Linear Fit

F/Ar = 0.17249 + 0.00153 Gas Flow (sccm)

Summary of Fit

| | |
|---|---|
| RSquare | 0.991784 |
| RSquare Adj | 0.98973 |
| Root Mean Square Error | 0.000915 |
| Mean of Response | 0.180879 |
| Observations (or Sum Wgts) | 6 |

Analysis of Variance

| Source | DF | Sum of Squares | Mean Square | F Ratio |
|---|---|---|---|---|
| Model | 1 | 0.00040397 | 0.000404 | 482.8533 |
| Error | 4 | 0.00000335 | 0.000001 | Prob > F |
| C Total | 5 | 0.00040732 | | <.0001 |

Parameter Estimates

| Term | Estimate | Std Error | t Ratio | Prob > |t| |
|---|---|---|---|---|
| Intercept | 0.1724864 | 0.000534 | 322.92 | <.0001 |
| Gas Flow (sccm) | 0.0015259 | 0.000069 | 21.97 | <.0001 |

These fit results demonstrate quantifying an unknown flow gas through the reaction chamber, utilizing measurements of intensity of the known spectral peaks of an unknown flow gas and a reference flow gas. In this instance, a linear fit of ratios of the spectral peaks was used. In another instance, a non-linear fit might be more appropriate. Or, a look up table could be indexed using the intensity measurements. The quantified flow of the unknown flow gas can, in turn, be used for process control. For instance, a mass flow controller can be recalibrated. Or, an endpoint can be detected based on a change in flow of the unknown flow gas.

Figure 12:
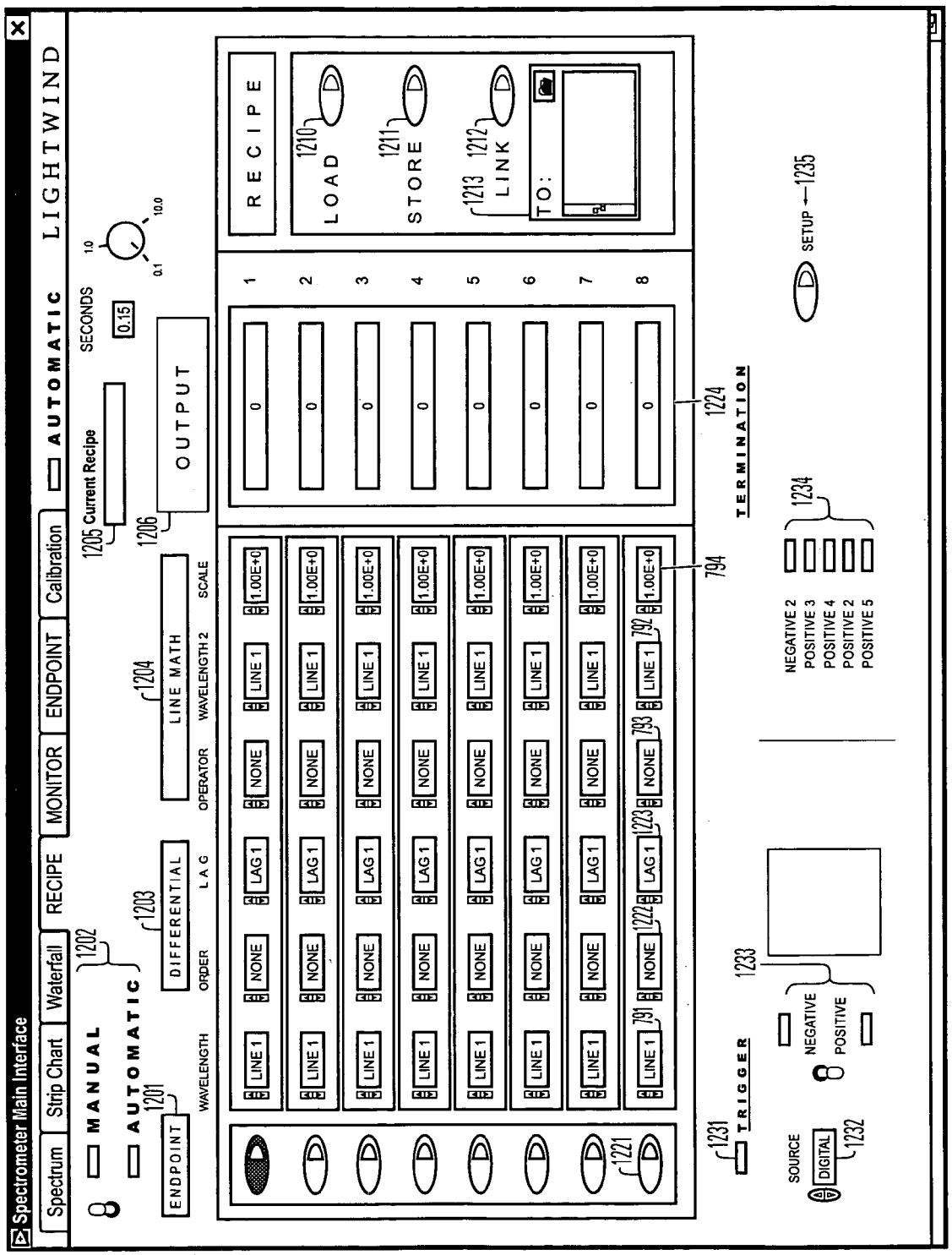
FIG. 12 is an interface for setting a recipe control.

FIG. 12 depicts an interface for setting a recipe that may be used to control a process step or series of process steps in a reaction chamber. Window 1201 indicates the type of process control. Endpoint, for instance, refers to detecting the completion of a process step. Switch 1202 and indicator lights for manual or automatic reflect the mode of operation for the recipe. In manual mode, the system signals a user, who responds to the signal. In automatic mode, the system generates a data output that is directly used to control the process. Many tools require an analog signal. Alternatively, a digital value, a SECS message or other protocol can be used to signal a tool. Windows 1203 and 1204 relate to the first and second wavelengths 791, 792 and related operators. Alternatively, instead of selecting particular wavelengths or band ranges, the results of other formula rows can selected. In addition, the whole spectrum can be selected, to operate on the whole brightness of the plasma. One or more formula rows for output to the tool that includes the reaction chamber are selected using buttons 1221. Operations can be performed on either data that is collected or differentials of data that is collected over time. Window 1203 selects a differential of the first wavelength 791. A first, second or other order differential can be selected using control 1222. A lag can be selected using control 1223. Window 1204 selects the value represented by the line for the second wavelength 792. The operator 793 indicates how the first and second wavelengths or outputs of other formula rows are combined, for instance, by mathematical or logical operators. The scaling factor 794 indicates the relative magnitude of the second wavelength that is combined with the first wavelength. In an alternative embodiment, the windows 1203, 1204 might select whether differential or line math were applied to the two wavelengths. The window 1205 allows for naming of a recipe. The button 1206 is for generation of output. The resulting output from combining the wavelengths in operators appears in window the 1224. Alternatively, during a setup mode invoked by control 1235, the window 1224 can be used to set a limit value. Controls 1210–1213 relate to the storage of the recipe. A recipe can be loaded using control 1210 or stored using control 1211. A plurality of recipes can be linked using the link button 1212 and the recipe name window 1213. These so-called recipes may correspond to process steps that combine into a tool recipe. The trigger indicator 1231 indicates whether a trigger has been set to initiate application of the displayed recipe. Trigger sources 1232 may be analog signals, digital signals, SECS or other protocol messages, the result of operating a prior recipe or any other trigger desired by the user. The controls 1233 indicate whether a negative signal going positive or a positive signal going negative is expected as a trigger. Alternatively, thresholds or limits could be used as triggers. Indicators 1234 are labeled to indicate a rising or falling trigger and, during operation, whether any of the triggers have been reached. This is useful to an operator or during startup of a system.

Figure 13:
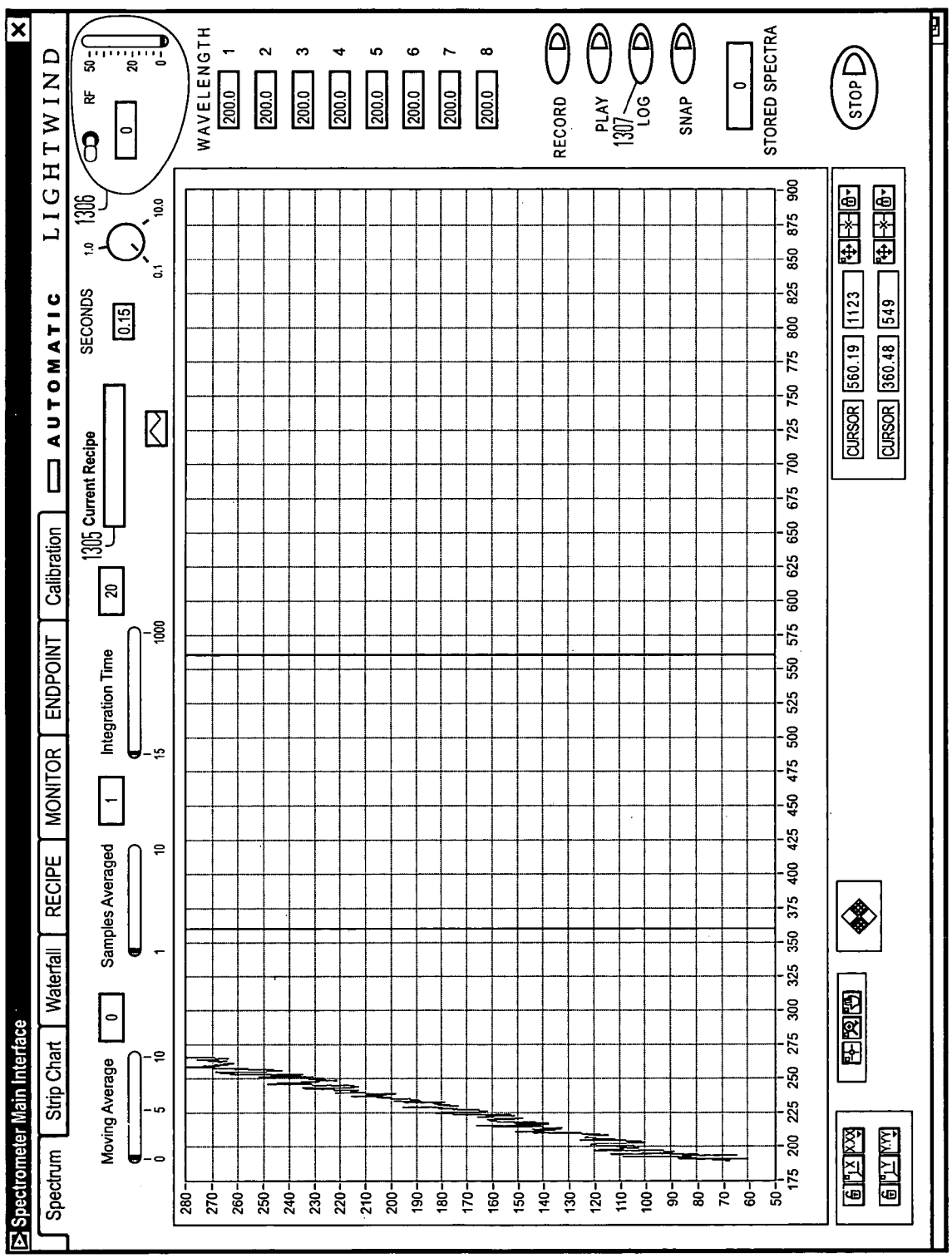
FIGS. 13–18 are an alternate embodiment of interfaces between the user and a system utilizing aspects of the present invention.

FIG. 13 is an alternate embodiment of the spectrum depicted in FIG. 5. A current recipe window 1305 and a log button 1307 are added. The current recipe window indicates the name of the current recipe that is running behind the recipe tab. The log button records spectrographic data at an interval set by the radio button in the top right hand corner of the figure. The log button is supplemented by a snap shot button, which enables a user to collect additional data between intervals for recording a log. Additional controls 1306 are provided, which relate to the power applied to generate plasma. In this figure, the power is off. The control depicted covers a power range of 0 to 50 watts. This range may represent a software lock on the dynamic range of the power supply that is used, so that only a fraction, for instance half, of the available power from the supply is ever used.

Figure 14:
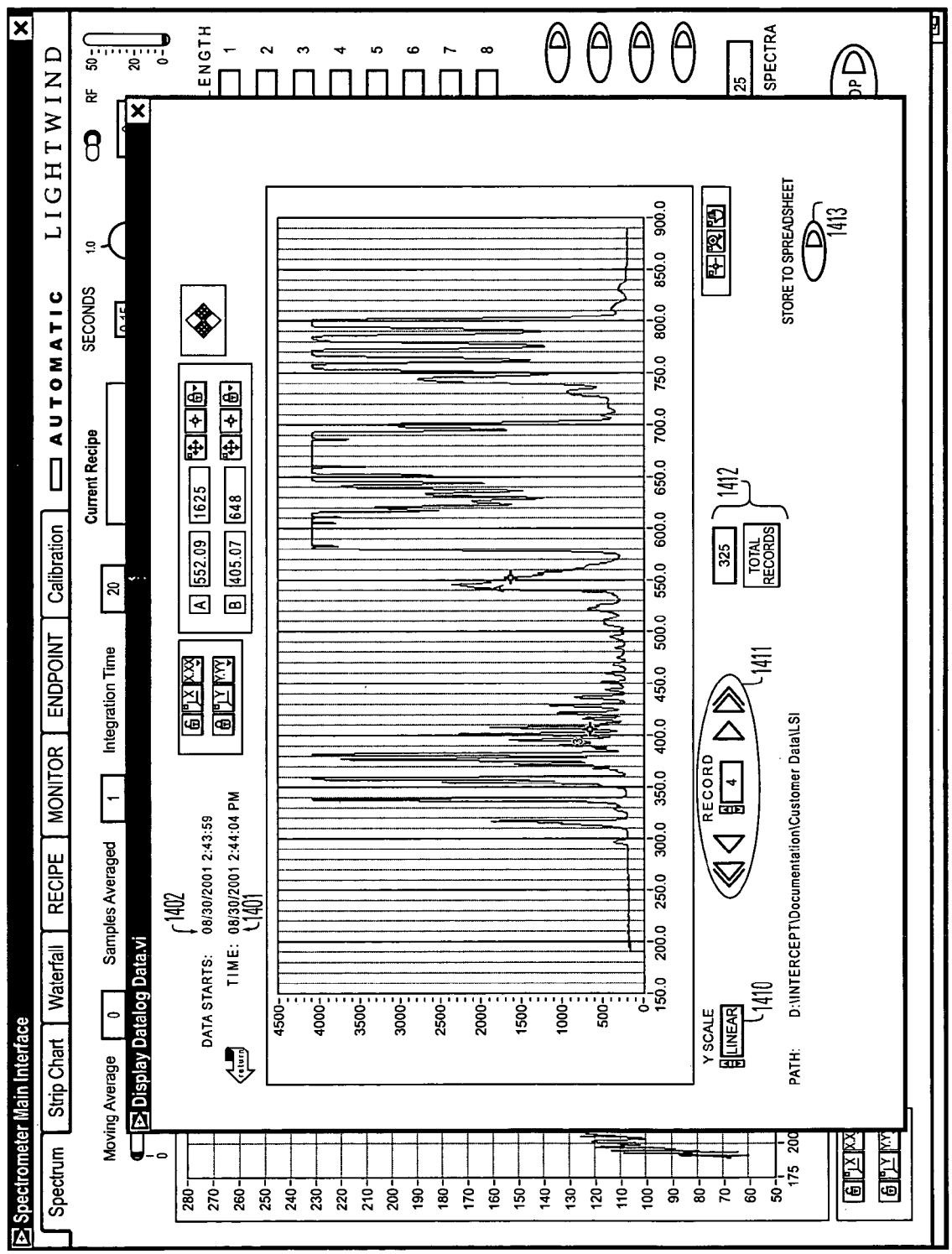

FIG. 14 depicts a play back of recorded data. The information and controls are generally is depicted in FIG. 5. In addition, starting date and time for the data set and a current date and time for the spectrograph displayed are indicated 1401, 1402. The vertical scale can be set to linear, logarithmic, or any other conventional use scale. Records selection controls and an indicator are provided 1411. The total number of records in the data set is indicated 1412. The options provided to store part or all of the data set in a spreadsheet 1413.

Figure 15:
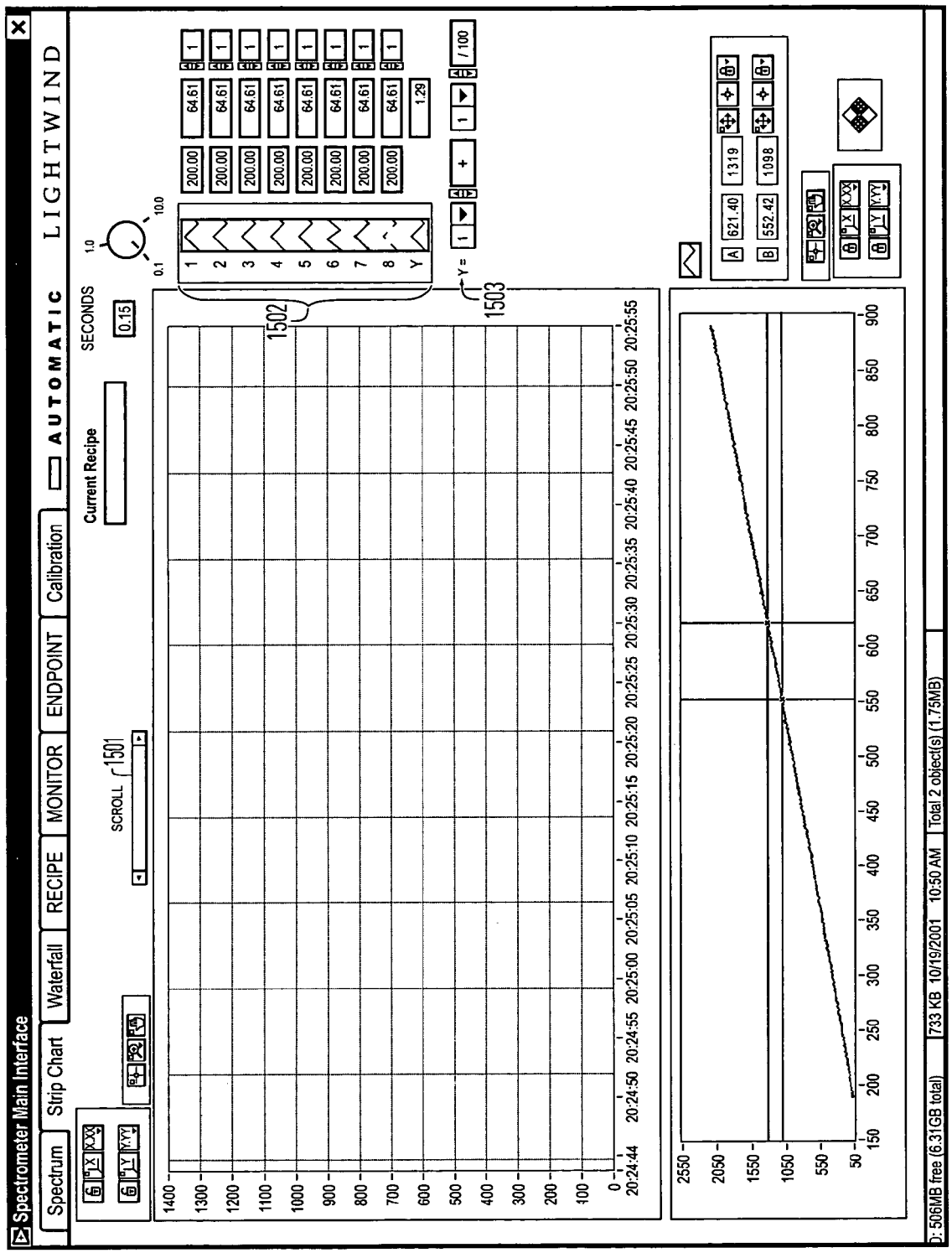

FIG. 15 is an alternate embodiment of the strip chart interface, FIG. 7. This embodiment adds a scroll control 1501 to move forward or backward through the data. Eight controls for generating graph lines data are provided, instead of six. Other alternative embodiments may provide for fewer than six or more than eight graph lines. The display for how the value y is calculated 1503, is improved.

Figure 16:
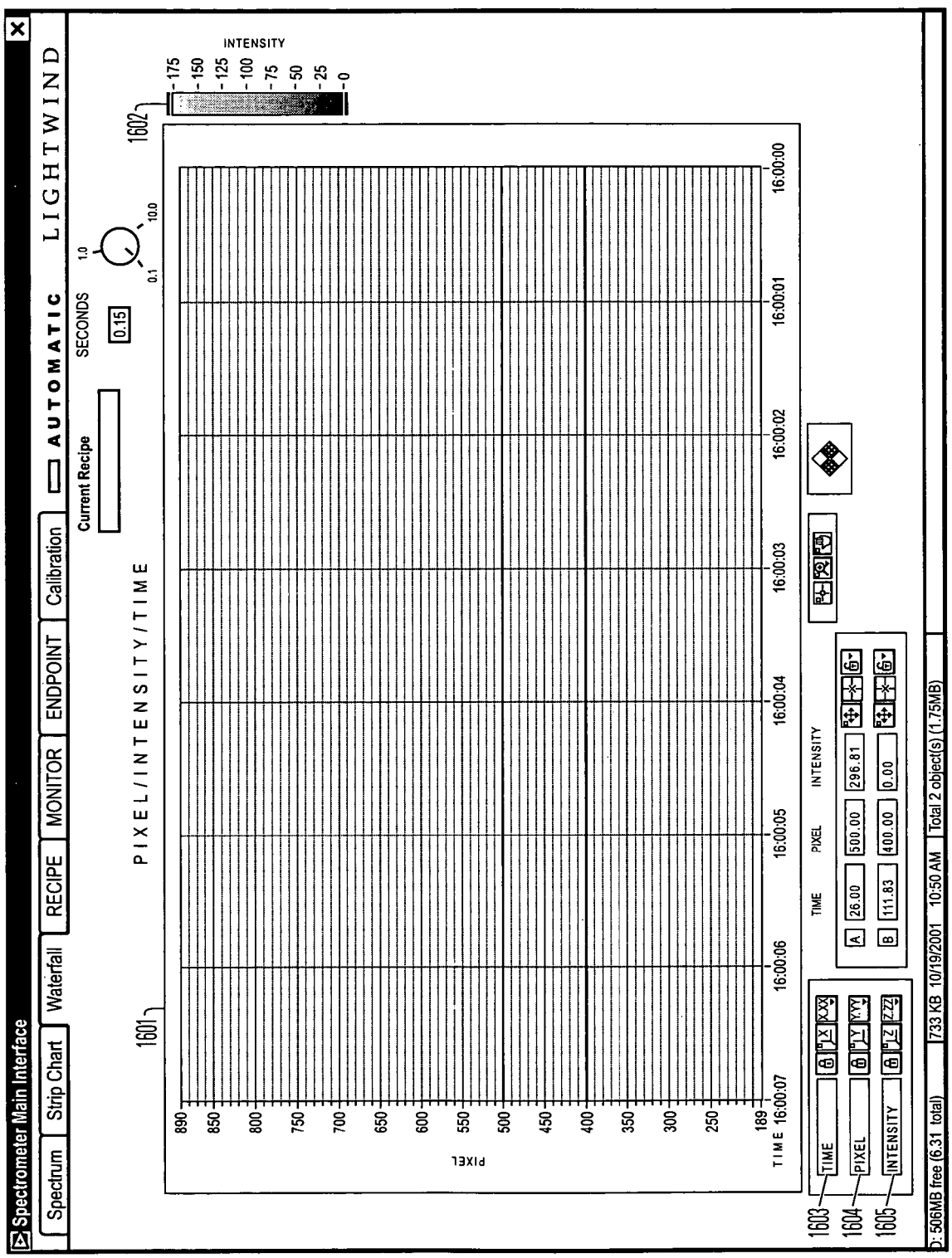

FIG. 16 is a pixel/intensity/time graph that depicts a history of the intensity of pixels in particular narrow bandwidths. The intensity scale 1602 indicates whether a saturated pixel will have a bright or dark value. The vertical axis of the field 1601 indicates the range of pixel values being displayed. The horizontal axis marks the time that is being displayed. In this display, the most recent time is on the left, though it could just as well be on the right.

Figure 17:
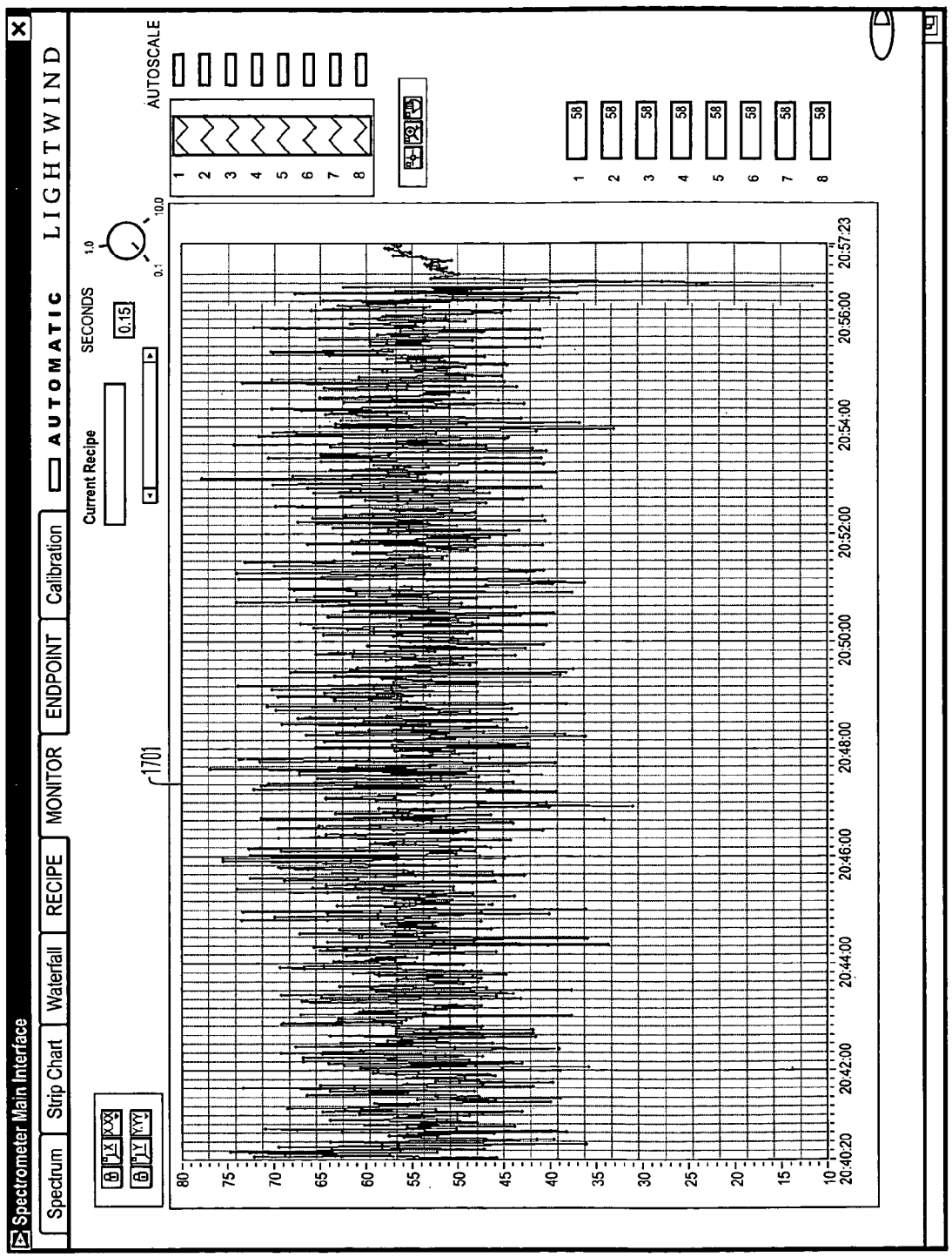

FIG. 17 is a monitor of output from formulas set up with the recipe tab, as in FIG. 12. It is a formula counterpart to the strip charts of FIGS. 7 and 15.

Figure 18:
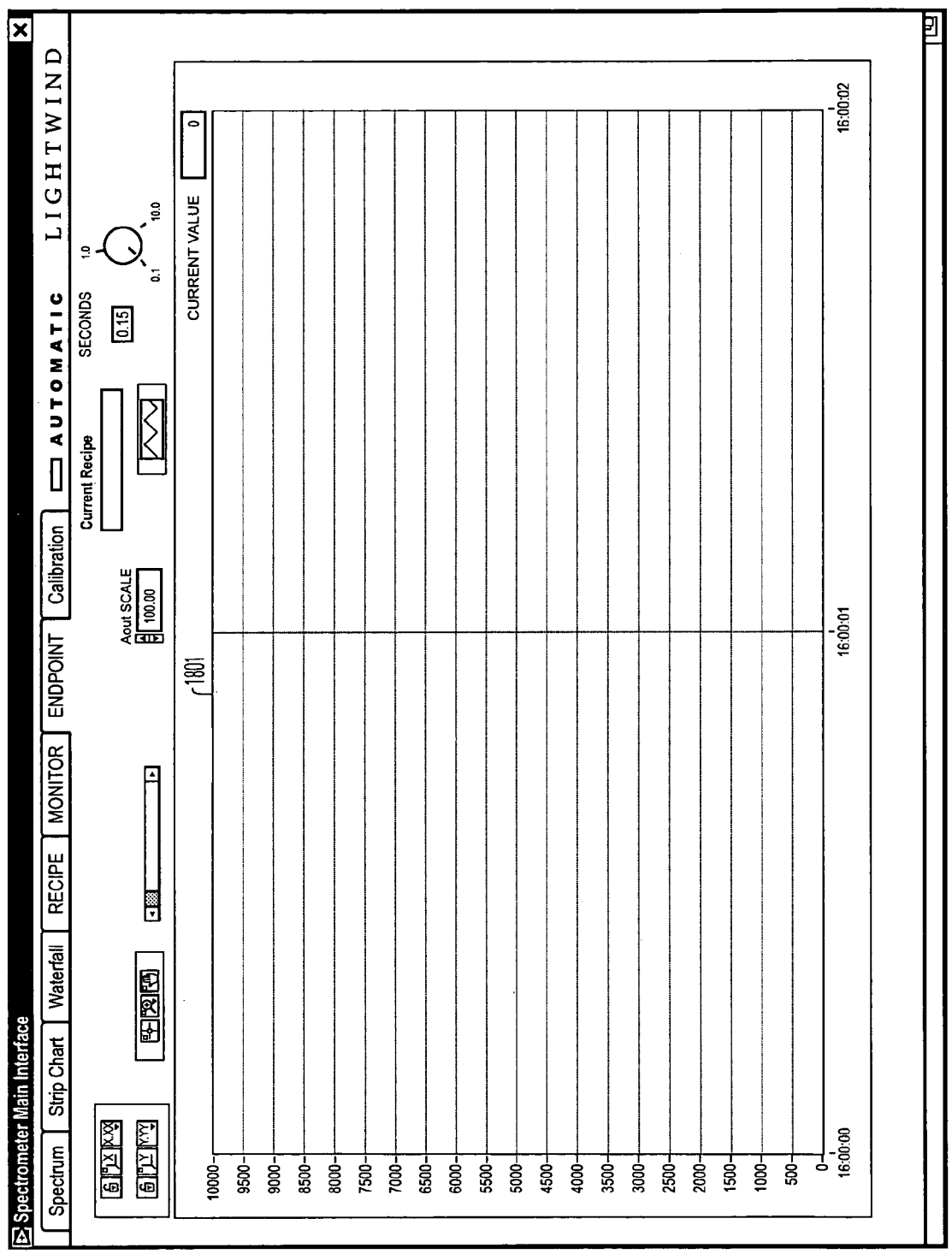

FIG. 18 is a real time monitor for a process approaching an endpoint. One or more lines can be displayed in the field 1801, which are set up using the recipe tab. The progress of recipe triggers toward limit values can be monitored in this field. The limit values can be indicated by horizontal lines set against the arbitrary vertical axis.

Aspects of the present invention include monitoring, analyzing and controlling a variety of processes. In reaction chambers, including chambers used for deposition, material diffuses into, builds up on or adsorbs to the reaction chamber walls that must be periodically cleaned or removed. During the use and cleaning cycle, the condition of the chamber walls can be analyzed and characterized as frequently as desired. The exhaust gas from the camber reflects the condition of the walls. When no reaction is taking place, chamber walls may off-gas or desorb materials that have diffused into, built up on or adsorbed to the chamber walls. The present invention includes analyzing exhaust gas while no process is taking place to characterize the condition of the chamber walls. For a plasma chamber, exposure of the chamber walls to active plasma leads to an equilibrium of materials added to and removed or released from the chamber walls. This equilibrium may change over time, more gradually when the plasma remains active than when the plasma is first energized. The present invention includes analyzing exhaust gas while plasma is active in the reaction chamber to characterize the condition of the chamber walls and to characterize the process itself. When a process is moved from one piece of equipment to another, for instance from one fab to another, it may be desirable to replicate the chamber conditioning that was used on the first piece of equipment. The present invention includes analyzing exhaust gas to characterize the first chamber and then analyzing exhaust gas to determine whether the second chamber conditions replicate the characteristics of the first chamber. During this replication effort, one aspect of the present invention is selecting and continuing a conditioning process to bring the second chamber conditions to a condition that resembles the characteristics of the first chamber. The conditioning process may be terminated, either by an operator or a closed loop process control when the second chamber conditions reach the desired parameters. Another aspect is modifying process conditions to compensate for differences between the characteristics of the first chamber and the second chamber conditions. As a process is propagated from one fab to another, experience teaches the kinds of process modifications that are appropriate to differing chamber conditions. The characteristics of a second chamber and second process instance may be analyzed and used to select appropriate process modifications.

Desorption of material from a chamber wall can be monitored using spectrographic techniques of the present invention. Adsorption is a rapid process in which a layer of $H_2O$, for instance, or many other gases adhere to a surface. At a water/silicon interface, for instance, a plurality of layers of water molecules are attracted to the interface. The layers closest to the interface are most strongly bound to the surface, as by van der Wal forces. The layers progressively further away from the interface are more loosely bound and behave more as a liquid layer. In processing, one technique for removing adsorbed layers is to pump down a piece of equipment, to apply a vacuum. Removal of adsorbed layers is sometimes inferred by closely monitoring pump down rates and chamber pressures. Certain pump down curves are characteristic of adsorbed layer removal. Utilizing aspects of the present invention, desorption can be directly monitored and rates estimated, if necessary, by ratioing one or more spectra of desorbed material to a reference material.

Diffusion or outgassing of material from a chamber wall can be monitored using spectrographic techniques of the present invention. Diffusion carries some materials, such as H2, into the chamber walls even thousands of layers deep. These materials may be removed by applying a vacuum, in some instances, and by flowing material through the chamber without activating a plasma, in other instances. The liberated or outgassed material may come from the surface of the chamber, in addition to the interior of the walls. For instance, fluorocarbon materials and polymers outgas from build-up on chamber walls. Utilizing aspects of the present invention, outgassing can be directly monitored and rates estimated, if necessary, by ratioing one or more spectra of outgassed material to spectra of a reference material.

Figure 11:
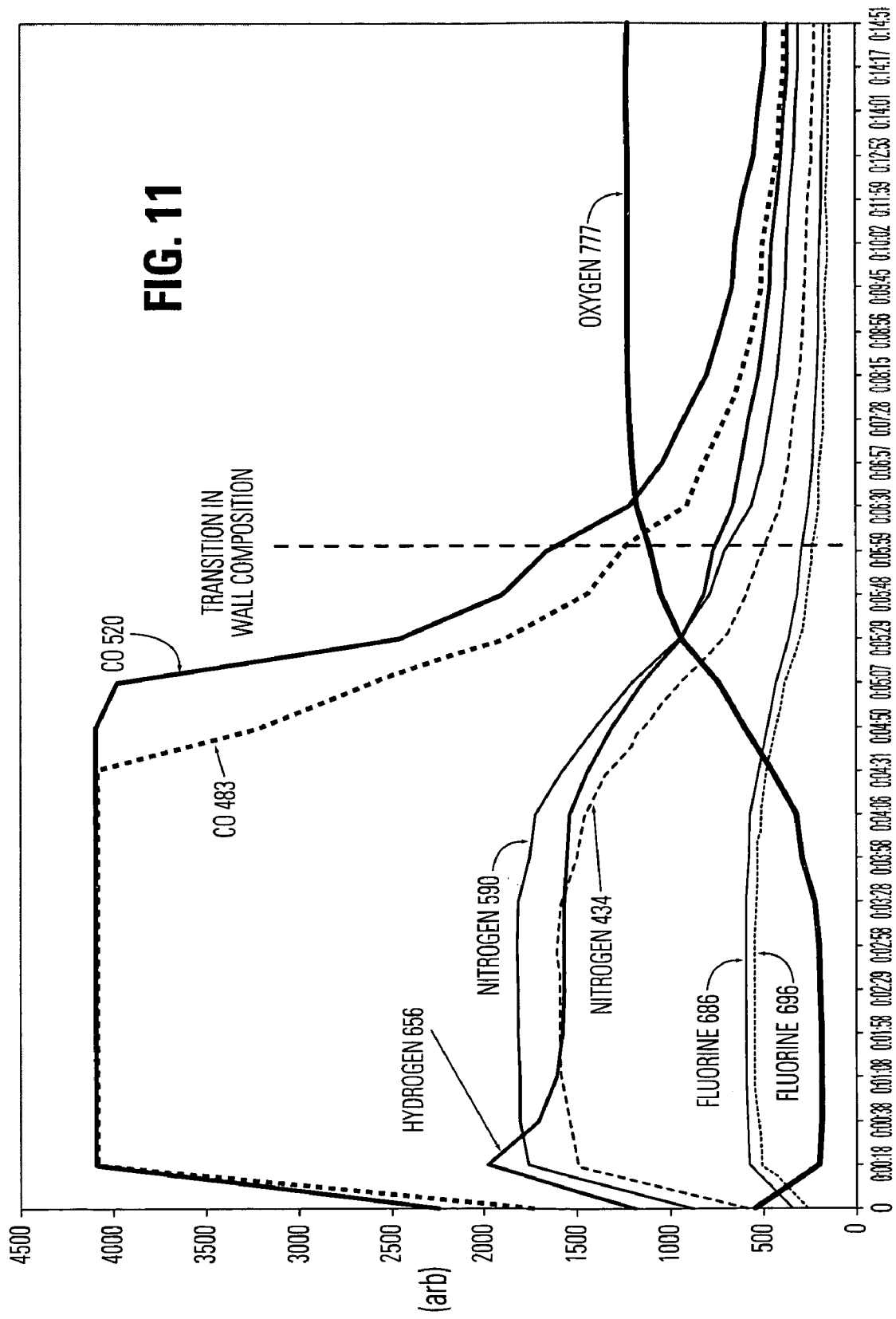
FIG. 11 depicts characterization of a reaction chamber during a cleaning process.

One technique for modifying the condition of a chamber includes using a plasma. Plasmas containing fluorine, hydrogen and/or oxygen are used to clean or condition the chamber walls. Running dummy or test wafers through the chamber with process materials often follows plasma cleaning. The dummy wafers may either be reactive or not. A build-up on chamber walls results from running the dummy wafers and process materials. These chamber wall conditioning processes are associated with characteristic emission lines for fluorine, carbon monoxide, oxygen, nitrogen, hydrogen, and other chemicals. Monitoring the intensity and changes in the intensity of peaks associated with plasmas of these process gases and byproducts allows an operator to see changes in the chamber wall chemistry and detect transitions in chamber conditioning. FIG. 11 depicts characterization of a reactor chamber during a cleaning process, including a transition in wall composition. This figure tracks cleaning of a reaction chamber with oxygen plasma for 14 minutes, 51 seconds. At approximately 5:29, the carbon monoxide production begins to drop steeply, as indicated by the peak centered at about 520 nm. At about the same time, oxygen concentration increases, as indicated by the peak centered at about 777 nm. The combination of decreased carbon monoxide production and increased oxygen concentration indicates a depletion of carbon from the chamber by the oxygen plasma. The depletion is believed to be an asymptotic process. The graph indicates that the carbon depletion process is reasonably complete at 11:59, 12:53 or 14:01. In this graph, the depletion of hydrogen, nitrogen and fluorine from the camber when exposed to oxygen plasma reaches a reasonable asymptotic value earlier than the depletion of carbon. Monitoring depletion of materials from a chamber during cleaning enables timing, control and validation of the cleaning process. Monitoring and characterization are not limited to a one step cleaning process. A plurality of cleaning and/or conditioning steps can be monitored in real time and produce a characterization of the chamber condition. One typical multi-step process involves use of a fluorine plasma to remove fluorinated residues, followed by an oxygen plasma, followed by a hydrogen plasma wall conditioning. The present invention includes multi-channel and full spectrum monitoring of a multi-step chamber cleaning and/or conditioning process. The monitoring may look for transitions in wall chemistry or a predetermined chamber condition, based on a profile of a prior chamber condition. The profile can include selected peaks, selected bands, or a full spectrum in a predetermined range. Analysis can be based, for instance, on peaks, spectral differences or asymptotic changes in peaks or spectral differences.

Plasma etch reactors experience a build up of polymers and other etch byproducts, which periodically must be cleaned or removed. A removal technique for these reaction chambers includes using plasmas containing oxygen or oxygen and fluorine, as described above. By monitoring the fluorine, carbon monoxide or other process gases or etch byproducts, it is practical to determine when the chamber is clean enough. Ending the cleaning process when the chamber is clean can reduce maintenance time or consumption of cleaning materials. It also can reproduce a desired chamber condition.

A reaction chamber that has been cleaned typically needs to be preprocessed and conditioned to develop a desirable build up of materials on or in the reaction chamber walls. This desirable build up restores process operation to a stable condition or at least to a known condition that is expected to produce predictable operating patterns. For instance, $H_2N_2$ is sometimes used to condition a chamber, resulting in diffusion of $H_2$ or $H^+$ into the chamber walls. Utilizing data from prior operations, desired byproduct levels and associated chamber wall conditions can be monitored, analyzed and used for process control. Conditioning of the reaction chamber can be allowed to proceed until the desired byproduct levels are met. Alternatively, conditioning of the reaction chamber can be allowed to proceed until the conditioning reaction reaches a steady state. Analysis of exhaust gas can be used to monitor, analyze or control the conditioning of a chamber.

Adaptation of processes from one type of process equipment to another may benefit from characterization of the established process. After characterizing the established process, a user can replicate the recorded process conditions as nearly as possible, before running production wafers. Manufacturer-neutral process baselines can be established, based on characterization of successful processes run on a variety of process equipment.

Reaction chambers sometimes produce environmentally sensitive byproducts. One environmentally sensitive byproduct that can be monitored, applying aspects of the present invention, is chlorinated fluorocarbons. These chlorinated fluorocarbons may include hydrochlorinated fluorocarbons. Either the exhaust of a wafer handling reaction chamber or a scrubber reaction chamber can be monitored for the presence of the environmentally sensitive byproducts. A process can be controlled to modify process conditions or to suspend processing when the level of environmentally sensitive chemicals exceeds an allowable threshold.

A generation of point of use exhaust gas processors has evolved to meet environmental concerns without compromising the flexible operation of tools. Capabilities of this type of equipment include thermal oxidation, chemisorption, wet treatment and integrated wet treatment/thermal oxidation. These systems are tailored to the processes run on specific tools and the exhaust gasses that result. In some instances, an abatement tool is dedicated to a particular process tool. Common to point of use systems is circulation of exhaust gasses to the house exhaust system. The present invention includes monitoring and validating exhaust gas from abatement tools.

Validation of exhaust from abatement tools involves measuring and recording concentrations of chemicals of concern in exhaust streams. For validation, sampling an exhaust stream of an abatement tool or a reaction chamber, preferably at below atmospheric pressure, is followed by generating plasma and a spectrum of the plasma. Actinometrical analyses can be applied to the spectrum of an exhaust stream to derive concentrations. In particular applications, it may be useful to add a reference gas of know properties, to generate spectral peaks for actinometrical analyses. In other applications, peaks of known process gases can be used for peak ratioing. Data can be collected using conventional methods that estimates the total gas flow of the sampled exhaust stream. Concentration data combined with gas flow data yields volume or mass flows of exhaust gas constituents. Useful aspects of the present invention include calculating and recording profiles, concentrations or exhaust mass flows from abatement tools. Calculated concentrations or flows can be used to trigger alarms, alerting either process control software or users to check the operation of certain equipment. Calculated volume or mass flows can be saved (or data for calculating the flows can be saved) as a history of exhaust from a particular abatement tool or reactor chamber. The historical data can be used to demonstrate to officials that progress has been made over time in reducing exhausts from particular reaction chambers, associated with the abatement tools. The historical data validates compliance with permits and commitments to progressively reduce certain exhausts over the life of a fab. It also allows a facility to back track from detection of an event at the centralized, house exhaust location to particular abatement tool(s) and reaction chamber(s) to determine when and where the intended process went wrong. This kind of failure analysis may utilize a system of spectrographic detectors at the exhausts of a plurality of reaction chambers and a plurality of abatement tools associated with the reaction chambers. A system of spectrographic systems with plasma sources can be used to feed data, in real time, to a server that monitors and/or records the data. A user with access to the same server can monitor processes and compliance with environmental regulations and commitments.

Reaction chambers that operate at pressures significantly below atmospheric pressure can be monitored for contamination with ambient or atmospheric gases. Such processes are susceptible to contamination from gases that leak into a vacuum chamber. The gases may contaminate sputtered films, alter etch chemistries, or degrade various processes in other ways. Spectral peaks can be monitored for the presence of nitrogen, oxygen or other gases present in atmospheric or clean room gases. Processes can be monitored and controlled so that detection of a leak suspends processing or a process sequence immediately or at the end of a process step.

The endpoint of a semiconductor process may be signaled by chemical state changes. For instance, when etching proceeds through a layer intended to be removed into a layer that is not supposed to be removed, the undesired etching produces different byproducts than the desired etching.

Spectral peaks can be monitored for decreases in desired byproducts and increases in undesired byproducts. Processes can be controlled so that etching stops when removal of a layer is sufficiently complete and before an underlying layer is excessively damaged.

Hardware failures in an etching reaction chamber produce detectable byproducts. For instance, ineffective clamping of a wafer tends to create elevated helium levels. Processes can be controlled so that the clamping of a wafer is adjusted before it is damaged and the process restarted from where it left off.

Generally speaking, chemical balances in a reaction chamber change during a process. By monitoring exhaust gas, estimates of the chemical concentrations in the chamber may be made and used to modify process parameters, such as parameters controlling the production of plasma in the reaction chamber.

By addition of a flow restrictor to the previously described embodiments, the equipment and methods of the present invention can be applied to sampling gases at or near atmospheric pressure. For instance, smokestack and tailpipe gases can be monitored. Compliance with emission control requirements can be monitored continuously. Industrial processes can be modified or suspended when emissions exceed allowable levels. Automobiles can be approved or disapproved for smog control, based on observed levels of emissions. The fuel/air mixture to an engine can be modified during operation, based on observed emission byproducts.

While the present invention is disclosed by reference to the embodiments and examples detailed above, it is understood that these examples are intended in an illustrative rather than in a limiting sense. It is contemplated that modifications and combinations will readily occur to those skilled in the art, which modifications and combinations will be within the spirit of the invention and the scope of the following claims. Each method practicing the present invention may readily be recast as a device or article of manufacture.

What is claimed is:

1. A method of semiconductor manufacturing in a reaction chamber to form a structure on a workpiece, the method including:
    depositing a layer over the workpiece, whereby at least a part of a structure is formed;
    while depositing the layer,
        sampling gas outside the reaction chamber that has passed through the reaction chamber during the depositing;
        exciting the sampled gas to emit radiation;
        detecting in real time from the radiation emitted a plurality of wave bands of an emission spectrum; and
        controlling the depositing in real time based on the detected wave bands.

2. The method of claim 1, wherein the dectecting step uses a spectrographic detector array that is sensitive to at least 512 wave bands.

3. The method of claim 1, wherein the dectecting step uses a spectrographic detector array that includes at least 512 detectors.

4. The method of claim 1, wherein characterizing in real time utilizes detectors responsive to band widths sufficiently narrow that a plurality of detectors are responsive to a single peak in the emission spectrum.

5. The method of claim 1, wherein characterizing in real time utilizes detectors responsive to the radiation emitted in 20 ms. or less.

6. A method of semiconductor manufacturing in a reaction chamber to form a structure on a workpiece, the method including:
    depositing a layer over the workpiece, whereby at least a part of a structure is formed;
    while depositing the layer, modifying operating parameters of the depositing responsive to a multi-band spectrographic analysis of exhaust gas from the reaction chamber.

7. A method of semiconductor manufacturing in a reaction chamber to form a structure on a workpiece, the method including:
    depositing a layer over the workpiece, whereby at least a part of a structure is formed;
    while depositing the layer, characterizing exhaust gas from the reaction chamber in real time utilizing a plasma source and a spectrographic detector array.

8. A method of semiconductor manufacturing in a reaction chamber to form a structure on a workpiece, the method including:
    etching away at least part of a layer over the workpiece, whereby at least a part of a structure is formed;
    while etching away the layer,
        sampling gas outside the reaction chamber that has passed through the reaction chamber during the depositing;
        exciting the sampled gas to emit radiation;
        detecting in real time from the radiation emitted a plurality of wave bands of an emission spectrum; and
        controlling the etching in real time based on the detected wave bands.

9. The method of claim 8, wherein the detecting step uses a spectrographic detector array that is sensitive to at least 512 wave bands.

10. The method of claim 8, wherein the dectecting step uses a spectrographic detector array that includes at least 512 detectors.

11. The method of claim 8, wherein characterizing in real time utilizes detectors responsive to band widths sufficiently narrow that a plurality of detectors are responsive to a single peak in the emission spectrum.

12. The method of claim 8, wherein characterizing in real time utilizes detectors responsive to the radiation emitted in 20 ms. or less.

13. A method of semiconductor manufacturing in a reaction chamber to form a structure on a workpiece, the method including:
    etching away at least part of a layer over the workpiece, whereby at least a part of a structure is formed;
    while etching away the layer, modifying operating parameters of the etching responsive to a multi-band spectrographic analysis of exhaust gas from the reaction chamber.

14. A method of semiconductor manufacturing in a reaction chamber to form a structure on a workpiece, the method including:
    etching away at least part of a layer over the workpiece, whereby at least a part of a structure is formed;
    while etching away the layer, characterizing exhaust gas from the reaction chamber in real time utilizing a plasma source and a spectrographic detector array.

15. A method of semiconductor manufacturing in a reaction chamber to form a structure on a workpiece, the method including:
    implanting into a layer over the workpiece, whereby at least a part of a structure is formed;
    while implanting into the layer, sampling gas outside the reaction chamber that has passed through the reaction chamber during the implanting;

exciting the sampled gas to emit radiation;

detecting in real time from the radiation emitted a plurality of wave bands of an emission spectrum; and controlling the implanting in real time based on the detected wave bands.

16. The method of claim 15, wherein the dectecting step uses a spectrographic detector array that is sensitive to at least 512 wave bands.

17. The method of claim 15, wherein the dectecting step uses a spectrographic detector array that includes at least 512 detectors.

18. The method of claim 15, wherein characterizing in real time utilizes detectors responsive to band widths sufficiently narrow that a plurality of detectors are responsive to a single peak in the emission spectrum.

19. The method of claim 15, wherein characterizing in real time utilizes detectors responsive to the radiation emitted in 20 ms. or less.

20. A method of semiconductor manufacturing in a reaction chamber to form a structure on a workpiece, the method including:

implanting into a layer over the workpiece, whereby at least a part of a structure is formed;

while implanting into the layer, modifying operating parameters of the implanting responsive to a multi-band spectrographic analysis of exhaust gas from the reaction chamber.

21. A method of semiconductor manufacturing in a reaction chamber to form a structure on a workpiece, the method including:

implanting into a layer over the workpiece, whereby at least a part of a structure is formed;

while implanting into the layer, characterizing exhaust gas from the reaction chamber in real time utilizing a plasma source and a spectrographic detector array.

* * * * *